(12) United States Patent
Case et al.

(10) Patent No.: US 8,388,204 B2
(45) Date of Patent: Mar. 5, 2013

(54) HIGH SPEED, HIGH RESOLUTION, THREE DIMENSIONAL SOLAR CELL INSPECTION SYSTEM

(75) Inventors: Steven K. Case, St. Louis Park, MN (US); Beverly Caruso, legal representative, St. Louis Park, MN (US); Carl E. Haugan, St. Paul, MN (US); Timothy A. Skunes, Mahtomedi, MN (US); Paul R. Haugen, Bloomington, MN (US); Eric P. Rudd, Hopkins, MN (US)

(73) Assignee: CyberOptics Corporation, Golden Valley, MN (US)

( * ) Notice: Subject to any disclaimer, the term of this patent is extended or adjusted under 35 U.S.C. 154(b) by 353 days.

(21) Appl. No.: 12/886,784

(22) Filed: Sep. 21, 2010

(65) Prior Publication Data

US 2011/0069154 A1 Mar. 24, 2011

Related U.S. Application Data

(63) Continuation-in-part of application No. 12/864,110, filed on Jan. 21, 2011, and a continuation-in-part of application No. 12/564,131, filed on Sep. 22, 2009.

(60) Provisional application No. 61/244,616, filed on Sep. 22, 2009, provisional application No. 61/244,671, filed on Sep. 22, 2009.

(51) Int. Cl.
*F21V 8/00* (2006.01)
(52) U.S. Cl. ........................ 362/551; 362/558
(58) Field of Classification Search .................. 362/551, 362/558, 560, 581
See application file for complete search history.

(56) References Cited

U.S. PATENT DOCUMENTS

| | | | |
|---|---|---|---|
| 1,577,388 A | 5/1923 | Twyman |
| 4,677,473 A | 6/1987 | Okamoto |
| 4,750,798 A | 6/1988 | Whitehead |
| 4,799,175 A | 1/1989 | Sano |
| 4,896,211 A | 1/1990 | Hunt |
| 4,978,224 A | 12/1990 | Kishimoto |
| 4,993,826 A | 2/1991 | Yoder |
| 5,039,868 A | 8/1991 | Kobayashi |
| 5,058,178 A | 10/1991 | Ray |

(Continued)

FOREIGN PATENT DOCUMENTS

| DE | 202008004430 | 1/2009 |
|---|---|---|
| EP | 0301255 | 2/1989 |

(Continued)

OTHER PUBLICATIONS

Martin, "A practical Guide to Machine Vision Lighting", Advance Illumination, Rochester, VT, United States, Oct. 2007.

(Continued)

*Primary Examiner* — David V Bruce
(74) *Attorney, Agent, or Firm* — Christopher R. Christenson; Westman, Champlin & Kelly, P.A.

(57) ABSTRACT

An optical inspection system and method are provided. A workpiece transport moves a workpiece in a nonstop manner. An illuminator includes a light pipe and is configured to provide a first and second strobed illumination field types. First and second arrays of cameras are arranged to provide stereoscopic imaging of the workpiece. The first array of cameras is configured to generate a first plurality of images of the workpiece with the first illumination field and a second plurality of images of the feature with the second illumination field. The second array of cameras is configured to generate a third plurality of images of the workpiece with the first illumination field and a fourth plurality of images of the feature with the second illumination field. A processing device stores at least some of the first, second, third, and fourth pluralities of images and provides the images to an other device.

47 Claims, 28 Drawing Sheets

U.S. PATENT DOCUMENTS

| | | | |
|---|---|---|---|
| 5,058,982 | A | 10/1991 | Katzir |
| 5,060,065 | A | 10/1991 | Wasserman |
| 5,086,397 | A | 2/1992 | Schuster |
| 5,153,668 | A | 10/1992 | Katzir |
| 5,245,421 | A | 9/1993 | Robertson |
| 5,260,779 | A | 11/1993 | Wasserman |
| 5,291,239 | A | 3/1994 | Jackson |
| 5,347,363 | A | 9/1994 | Yamanaka |
| 5,445,870 | A | 8/1995 | Buchner |
| 5,517,234 | A | 5/1996 | Gerber |
| 5,550,583 | A | 8/1996 | Amir |
| 5,684,530 | A | 11/1997 | White |
| 5,696,591 | A | 12/1997 | Bilhorn |
| 5,822,055 | A | 10/1998 | Tsai |
| 5,825,495 | A | 10/1998 | Huber |
| 5,880,772 | A | 3/1999 | Kalnajs |
| 6,023,663 | A | 2/2000 | Kim |
| 6,175,107 | B1 | 1/2001 | Juvinall |
| 6,222,624 | B1 | 4/2001 | Yonezawa |
| 6,362,877 | B1 | 3/2002 | Kobayashi |
| 6,577,405 | B2 | 6/2003 | Kranz |
| 6,633,375 | B1 | 10/2003 | Veith |
| 6,757,966 | B2 | 7/2004 | Inoue |
| 6,850,855 | B2 | 2/2005 | Kawai |
| 7,019,826 | B2 | 3/2006 | Vook |
| 7,075,565 | B1 | 7/2006 | Raymond |
| 7,310,438 | B2 | 12/2007 | Prince |
| 7,460,219 | B2 | 12/2008 | Jung |
| 7,828,472 | B2 | 11/2010 | Liu |
| 2002/0089664 | A1 | 7/2002 | Shibata |
| 2003/0039388 | A1 | 2/2003 | Ulrich et al. |
| 2003/0110610 | A1 | 6/2003 | Duquette et al. |
| 2003/0179369 | A1 | 9/2003 | Feldman |
| 2003/0227618 | A1 | 12/2003 | Some |
| 2004/0156539 | A1 | 8/2004 | Jansson |
| 2005/0219518 | A1 | 10/2005 | Korngut |
| 2005/0259245 | A1 | 11/2005 | Cemic |
| 2006/0062013 | A1 | 3/2006 | Imade |
| 2011/0069507 | A1 | 3/2011 | Haugan |
| 2011/0069878 | A1 | 3/2011 | Case |
| 2011/0090333 | A1 | 4/2011 | Haugan |
| 2011/0102575 | A1 | 5/2011 | Case |
| 2011/0175997 | A1 | 7/2011 | Case |
| 2012/0133920 | A1* | 5/2012 | Skunes et al. .......... 356/23 |

FOREIGN PATENT DOCUMENTS

| | | |
|---|---|---|
| EP | 0994646 | 4/2000 |
| EP | 1578186 | 9/2005 |
| EP | 1694109 A2 | 2/2006 |
| GB | 2271683 | 4/1994 |
| GB | 2417072 | 2/2006 |
| GB | 2444409 | 6/2008 |
| JP | 61134718 | 6/1986 |
| JP | 62298750 | 12/1987 |
| JP | 63011842 | 1/1988 |
| JP | 02268260 | 11/1990 |
| JP | 08327561 | 12/1996 |
| JP | 2002271099 A | 9/2002 |
| JP | 2006324599 | 11/2006 |
| WO | WO98/19200 A1 | 5/1998 |
| WO | WO 00/26640 | 5/2000 |
| WO | WO 00/38494 | 6/2000 |
| WO | WO 01/96839 | 12/2001 |
| WO | WO 2009/014940 | 1/2009 |

OTHER PUBLICATIONS

Scharstein and Szeliski, "A Taxonomy and Evaluation of Dense Two-Frame Stereo Correspondence Algorithms"Microsoft Research, Microsoft Corporation, Redmond, WA.

Smith, "Modern Optical Engineering: The Design of Optical Systems", 4th ed. New York: McGraw-Hill, 2008.

Kang,Web, Zitinick, and Takeo, "A Multibaseline Stereo System with Active Illumination and Real-time Image Acquisition."

Collins, "A Space-Sweep Approach to True Multi-Image Matching" University of Massachusetts, Amherst, MA.

CyberOptics, "Flex Ultra TM HR, Automated Optical Inspection", CyberOptics Corporation 2007.

Notification of transmittal of the International Search Report and the Written Opinion for International application No. PCT/US2009/031744 dated May 18, 2009.

Notification of transmittal of the International Search Report and the Written Opinion for International application No. PCT/US2010/049619 dated Dec. 8, 2010.

Notification of transmittal of the International Search Report and the Written Opinion for International application No. PCT/US2010/04617 dated Dec. 8, 2010.

Notification of transmittal of the International Search Report and the Written Opinion for International application No. PCT/US2010/055452 dated Jan. 17, 2011.

U.S. Appl. No. 12/864,110, filed Jul. 22, 2010.

U.S. Appl. No. 12/940,214, filed Nov. 5, 2010.

U.S. Appl. No. 12/564,131, filed Sep. 22, 2009.

U.S. Appl. No. 12/886,803, filed Sep. 21, 2010.

U.S. Appl. No. 12/939,267, filed Nov. 4, 2010.

Written Opinion for International application No. PCT/US2010/049617 dated Feb. 14, 2012.

Notification of Transmittal of International Preliminary Report on Patentability for the International application No. PCT/US10/49617 dated Aug. 24, 2012.

Notification of transmittal of the International Search Report and the Written Opinion for International application No. PCT/US2011/059040 dated Jul. 20, 2012.

Invitation to Pay Additional Fees from International patent application No. PCT/US2011/059040 dated Mar. 15, 2012.

Related U.S. Appl. No. 13/480,079, filed May 24, 2012.

* cited by examiner

HIGH SPEED, HIGH RESOLUTION, THREE DIMENSIONAL SOLAR CELL INSPECTION SYSTEM

CROSS-REFERENCE TO RELATED APPLICATION

The present application is based on and claims the benefit of U.S. Provisional Application Ser. No. 61/244,616, filed Sep. 22, 2009 and U.S. Provisional Application Ser. No. 61/244,671, filed on Sep. 22, 2009; the present application is a Continuation-In-Part application of U.S. patent application Ser. No. 12/864,110 filed Jan. 21, 2011; and the present application is a Continuation-In-Part application of U.S. patent application Ser. No. 12/564,131, filed Sep. 22, 2009. All applications listed above are herein incorporated by reference in their entireties.

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Advancements in automated photovoltaic solar cell manufacturing are enabling higher throughput, yield, and cell conversion efficiencies. For example, commercially available automated equipment for applying conductive layers to crystalline silicon solar cells routinely screen print the metallization at a rate of one cell per second. Newer technologies for improving cell conversion efficiencies such as the selective emitter process, metal-wrap-through, and print-on-print are being adopted that require precise registration of the metallization layers. Cell efficiencies are also affected by the height to width ratio of the metalized collector fingers, which collect the electric current generated by the solar cell. These fingers must be printed narrowly in width to avoid unnecessary shading of the cell active area, but must also be printed tall in height to improve electrical conductivity. Also, the fragility of the thin silicon solar cells and their tendency to bow during manufacturing, presents challenges to the automated handling equipment to avoid chips and cracks. Bowed wafers may crack, for example, when they are vacuum secured during one of the many manufacturing process steps or when pressure is applied to the wafer during the screen printing process. In view of these industry demands, a need has arisen for automated optical inspection systems that are distributed throughout the solar cell manufacturing process to ensure high process yield. Given the increased needs for precision registration, narrower and taller features, and detection of wafer bowing, it would be beneficial to provide an automated optical inspection system that was not only faster than the prior art, but also better able to provide higher resolution two and three dimensional inspection of the solar cells.

SUMMARY

An optical inspection system and method are provided. A workpiece transport is configured to transport a workpiece in a nonstop manner. An illuminator is configured to provide a first strobed illumination field type and a second strobed illumination field type. The illuminator includes a light pipe having a first end proximate the workpiece, and a second end opposite the first end and spaced from the first end. The light pipe also has at least one reflective sidewall. The first end has an exit aperture and the second end has at least one second end aperture to provide a view of the workpiece therethrough. A first array of cameras is configured to digitally image the workpiece. The first array of cameras is configured to generate a first plurality of images of the workpiece with the first illumination field and a second plurality of images of the feature with the second illumination field. A second array of cameras configured to digitally image workpiece. The second array of cameras is configured to generate a third plurality of images of the workpiece with the first illumination field and a fourth plurality of images of the feature with the second illumination field. The first and second arrays of cameras are configured to provide stereoscopic imaging of the workpiece. A processing device is operably coupled to the illuminator and the first and second arrays of cameras. The processing device is configured to store at least some of the first, second, third, and fourth pluralities of images and provide the first, second, third and fourth pluralities of images to an other device.

DETAILED DESCRIPTION OF ILLUSTRATIVE EMBODIMENTS

Embodiments of the present invention generally provide a compact inspection system and method with high speed acquisition of multiple illumination two and three dimensional images without the need for expensive and sophisticated motion control hardware. Processing of the images acquired with different illumination types may appreciably enhance the inspection capabilities and results.

Figure 1:
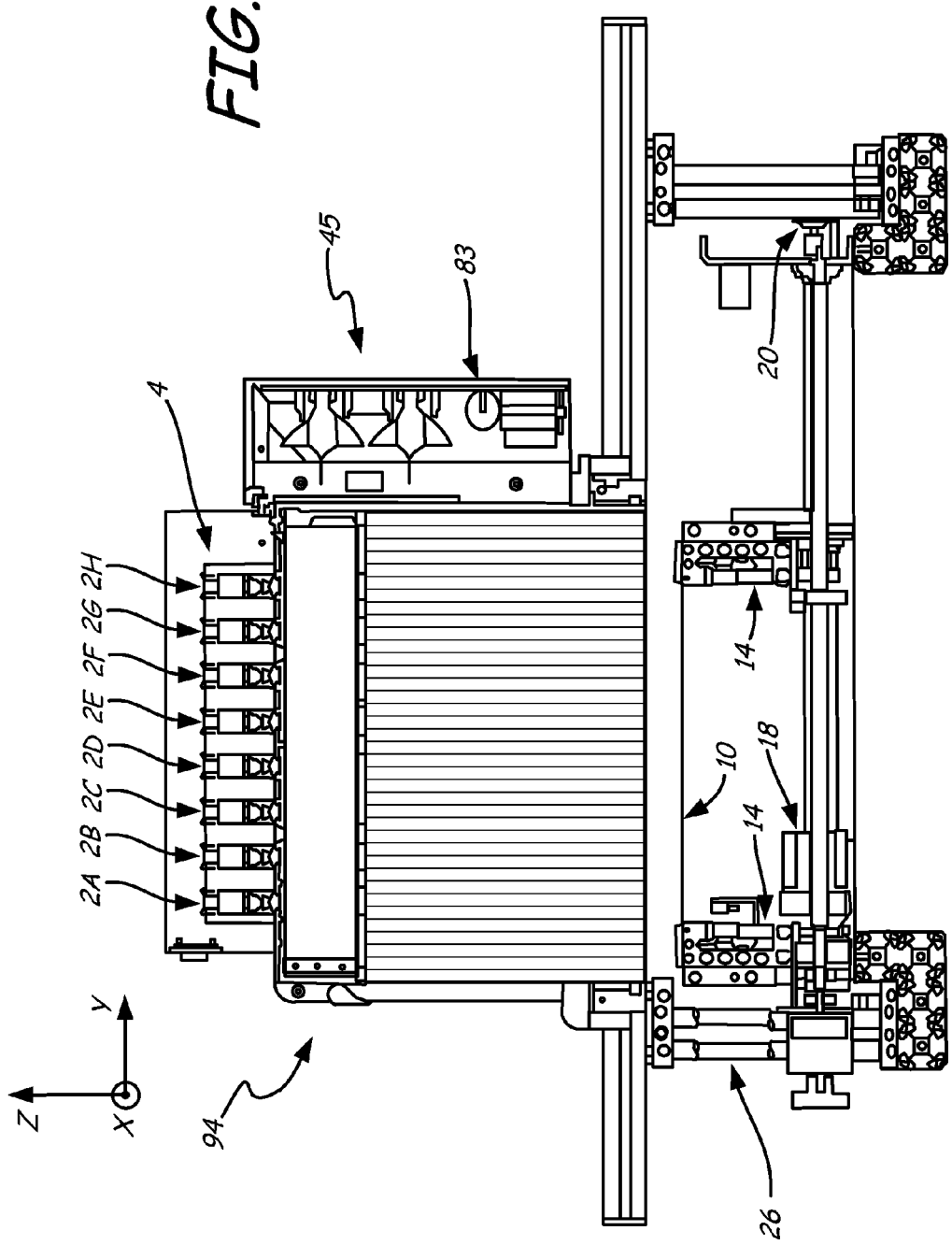
FIG. 1 is a cross-sectional elevation view of an automated high speed optical inspection system with a camera array and compact, integrated illuminator in accordance with embodiment of the present invention.

FIG. 1 shows a cross-sectional elevation view of a system for generating high contrast, high speed digital images of a workpiece that are suitable for automated inspection, in accordance with an embodiment of the present invention. Camera array 4 consists of cameras 2A through 2H preferably arranged at regular intervals. Each camera 2A through 2H simultaneously images and digitizes a rectangular area on a workpiece or substrate, such as silicon photovoltaic solar cell 12, while the workpiece undergoes relative movement with respect to cameras 2A through 2H. Illuminator 45 provides a series of pulsed, short duration illumination fields referred to as strobed illumination. The short duration of each illumination field effectively "freezes" the image of solar cell 12 to suppress motion blurring. Two or more sets of images for each location on solar cell 12 are generated by camera array 4 with different illumination field types for each exposure. Depending on the particular features on solar cell 12 that need to be inspected, the inspection results may be appreciably enhanced by joint processing of the reflectance images generated with different illumination field types. Further details of illuminator 45 are provided in the discussion of FIGS. 21 and 22.

Figure 2:
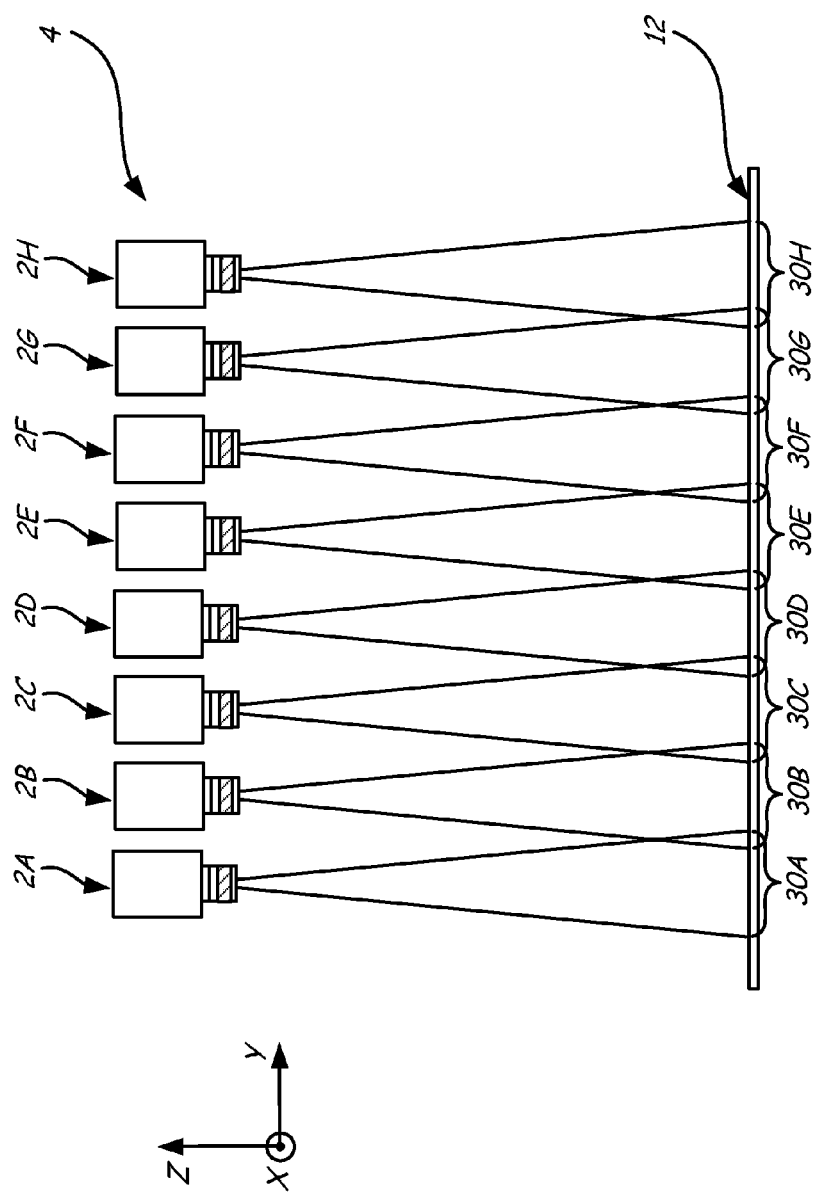
FIG. 2 is a diagrammatic elevation view of a plurality of cameras having overlapping fields of view in accordance with an embodiment of the present invention.

Workpiece transport conveyor 26 translates solar cell 12 in the X direction in a nonstop mode to provide high speed imaging of solar cell 12 by camera array 4. Conveyor 26 includes belts 14 which are driven by motor 18. Optional encoder 20 measures the position of the shaft of motor 18 hence the approximate distance traveled by solar cell 12 can be calculated. Other methods of measuring and encoding the distance traveled of solar cell 12 include time-based, acoustic or vision-based encoding methods. By using strobed illumination and not bringing solar cell 12 to a stop, the time-consuming transport steps of accelerating, decelerating, and settling prior to imaging by camera array 4 are eliminated. It is believed that the time required to entirely capture two complete 80 megapixel images of solar cell 12 of dimensions 156 mm×156 mm, with two illumination field types, can be accomplished in approximately one second or less FIG. 2 shows the Y dimension location of each field of view 30A through 30H on solar cell 12 that is imaged by cameras 2A through 2H, respectively. There is a slight overlap between adjacent fields of view in order to completely image all locations on solar cell 12. During the inspection process, the images of discrete fields of view 30A through 30H are digitally merged, or stitched, into one continuous image in the overlap regions. Example camera array 4 is shown in FIGS. 1 and 2 arranged as a single dimensional array of discrete cameras. As shown, cameras 2A-2H are configured to image in a non-telecentric manner. This has the advantage that the fields of view 30A through 30H can be overlapped. However, the magnification, or effective resolution, of a non-telecentric imaging system will change as solar cell 12 thickness varies as well as the amount of bowing. Effects of solar cell 12 warpage, thickness variations and other camera alignment errors can be compensated by image stitching. In another embodiment, the camera array may be arranged in a two dimensional array. For example, the discrete cameras may be arranged into a camera array of two columns of four cameras where adjacent fields of view overlap. Other arrangements of the camera array may be advantageous depending on cost, speed, and performance goals of the inspection system, including arrays where the fields of view do not overlap. For example, a staggered array of cameras with telecentric imaging systems may be used.

Figure 3:
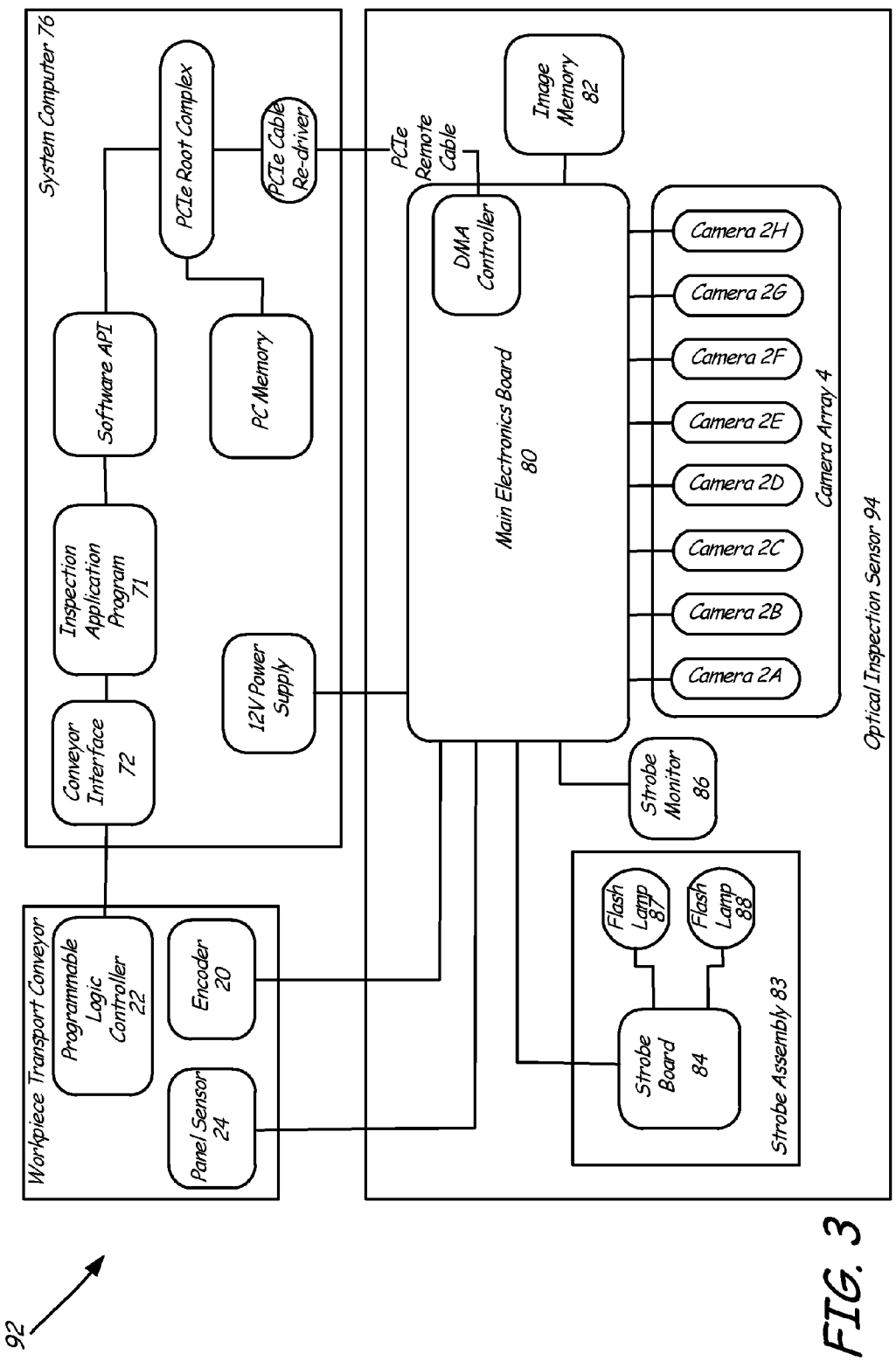
FIG. 3 is a system block diagram of an inspection system in accordance with an embodiment of the present invention.

FIG. 3 is a block diagram of inspection system 92. Inspection application program 71 preferably executes on system computer 76. Inputs into inspection program 71 include, for example, solar cell 12 geometry, metallization print geometry, and inspection tolerance limits for print defects, color defects, edge chipping, microcrack size, and saw marks. Lighting and camera calibration data may also be input to inspection program 71.

Inspection program 71 configures programmable logic controller 22 via conveyor interface 72 with the transport direction and velocity of solar cell 12. Inspection program 71 also configures main electronics board 80 via PCI express interface with the number of encoder 20 counts between each subsequent image acquisition of camera array 4. Alternatively, a time-based image acquisition sequence may be executed based on the known velocity of solar cell 12. Inspection program 71 also programs or otherwise sets appropriate configuration parameters into cameras 2A-2H prior to an inspection as well as strobe board 84 with the individual flash lamp output levels.

Panel sensor 24 senses the edge of solar cell 12 as it is loaded into inspection system 92 and this signal is sent to main board 80 to begin an image acquisition sequence. Main board 80 generates the appropriate signals to begin each image exposure by camera array 4 and commands strobe board 84 to energize the appropriate flash lamps 87 and 88 at the proper time. Strobe monitor 86 senses a portion of light emitted by flash lamps 87 and 88 and this data may be used by main electronics board 80 to compensate image data for slight flash lamp output variations. Image memory 82 is provided and preferably contains enough capacity to store all images generated for at least one solar cell 12. For example, in one embodiment, each camera in the array of cameras has a resolution of about 5 megapixels and memory 82 has a capacity of about 2.0 gigabytes. Image data from cameras 2A-2H may be transferred at high speed into image memory buffer to allow each camera to be quickly prepared for subsequent exposures. This allows solar cell 12 to be transported through inspection system 92 in a nonstop manner and generate images of each location on solar cell 12 with at least two different illumination field types. The image data may begin to be read out of image memory 82 into PC memory over a high speed electrical interface such as PCI Express (PCIe) as soon as the first images are transferred to memory 82. Similarly, inspection program 71 may begin to compute inspection results as soon as image data is available in PC memory.

The image acquisition process will now be described in further detail with respect to FIGS. 4-6.

Figure 4:
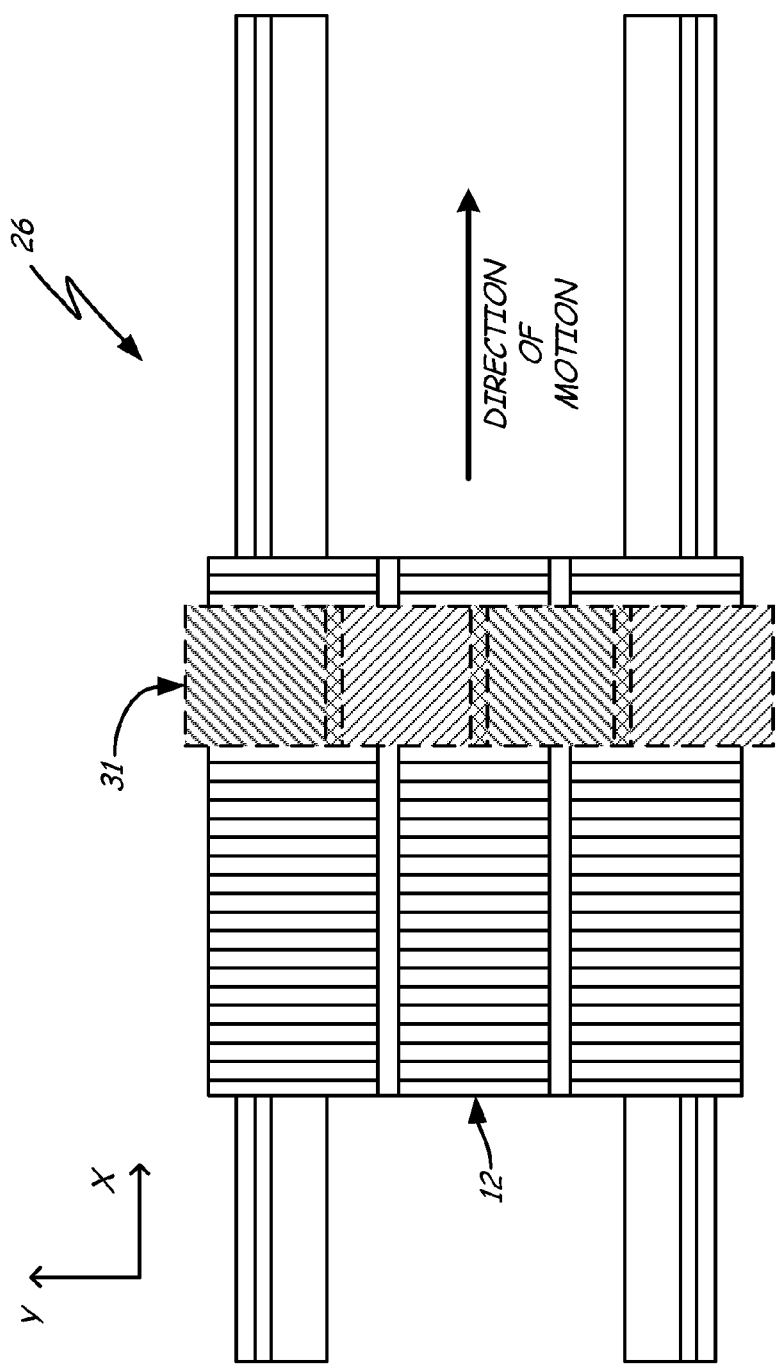
FIG. 4 is a top plan view of a transport conveyor, solar cell, and a camera array field of view acquired with a first illumination field type.

FIG. 4 shows a top plan view of transport conveyor 26 and solar cell 12. Cameras 2A-2H image overlapping fields of view 30A-30H, respectively, to generate effective field of view 32 of camera array 4. Field of view 32 is acquired with a first strobed illumination field type. Solar cell 12 is transported by conveyor 26 in a nonstop manner in the X direction. Solar cell 12 preferably travels at a velocity that varies less than five percent during the image acquisition process, although larger velocity variations and accelerations may be accommodated.

In one preferred embodiment, each field of view 30A-30H has approximately 5 million pixels with a pixel resolution of 17 microns and an extent of 34 mm in the X direction and 45 mm in the Y direction. Each field of view 30A-30H overlaps neighboring fields of view by approximately 3 mm in the Y direction so that center-to-center spacing for each camera 2A-2H is 42 mm in the Y direction. In another embodiment, camera array 4 consists of only 4 cameras 2A-2D. In this embodiment, camera array field of view 32 has a large aspect ratio in the Y direction compared to the X direction of approximately 5:1.

Figure 5:
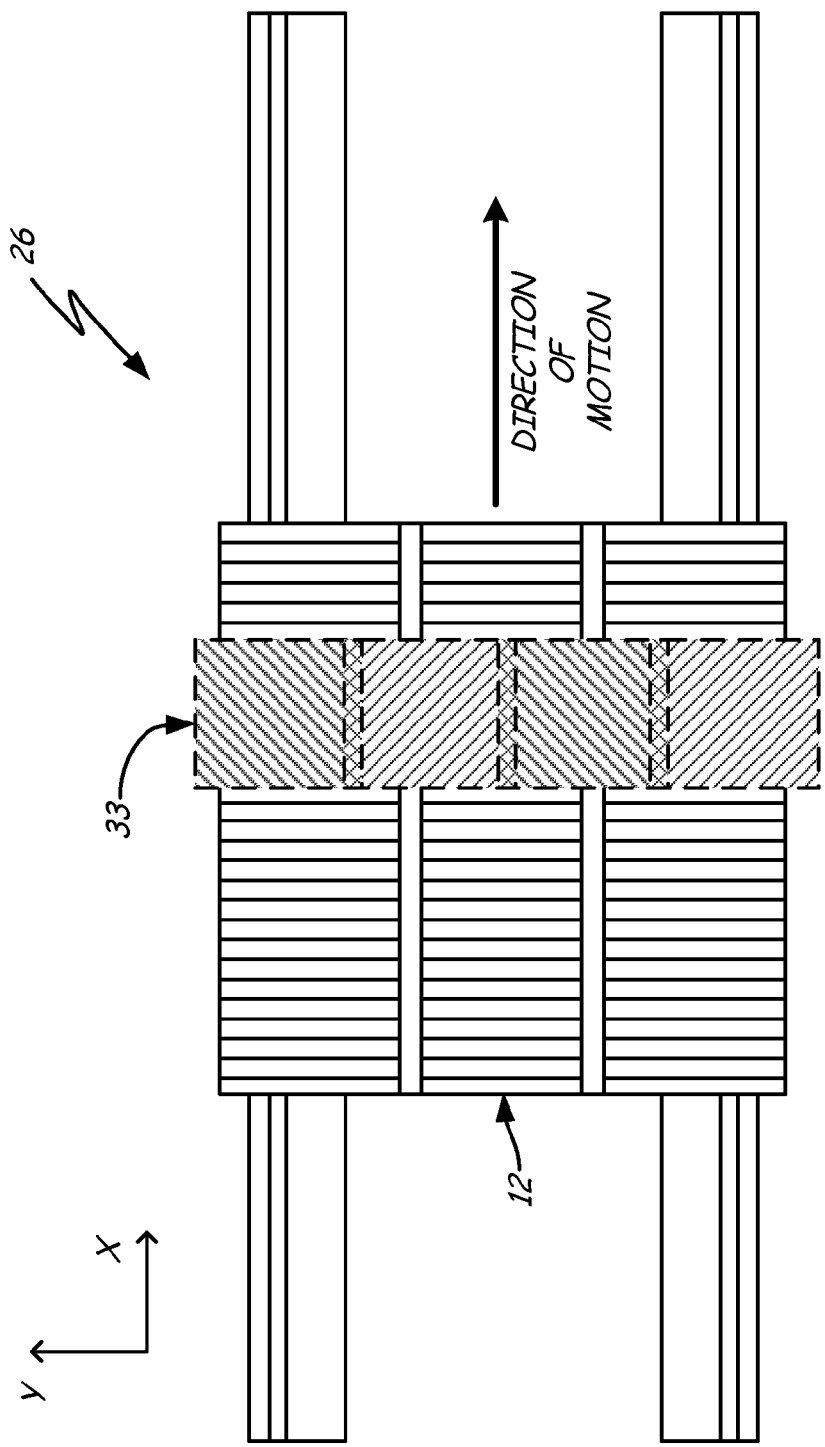
FIG. 5 is a top plan view of a transport conveyor, solar cell, and a camera array field of view acquired with a second illumination field type.

FIG. 5 shows solar cell 12 at a location displaced in the positive X direction from its location in FIG. 4. For example, solar cell 12 may be advanced approximately 15 mm from its location in FIG. 4. Effective field of view 33 is composed of overlapping fields of view 30A-30D and is acquired with a second illumination field type.

Figure 6A:
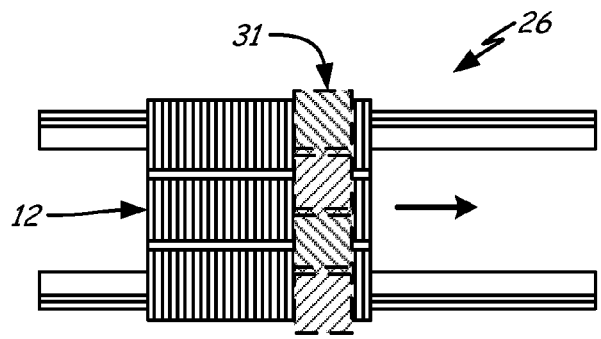
FIGS. 6A-6D illustrate a workpiece and camera array fields of view acquired at different positions and under alternating first and second illumination field types in accordance with an embodiment of the present invention.
Figure 6B:
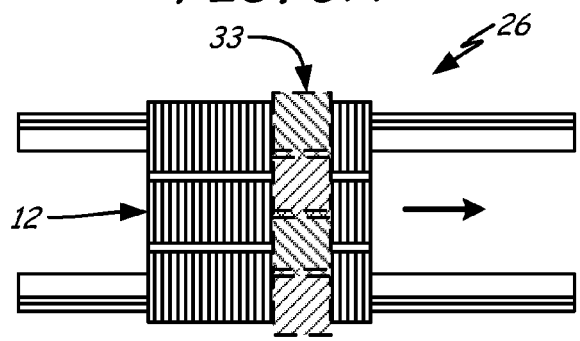
Figure 6C:
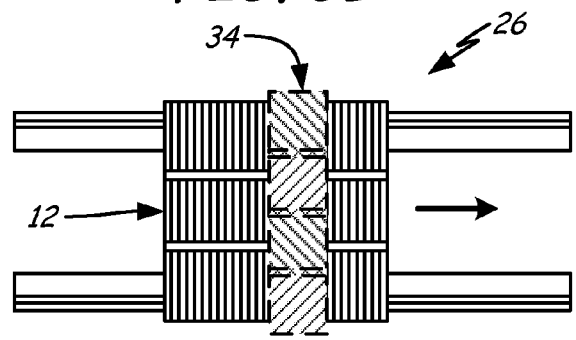
Figure 6D:
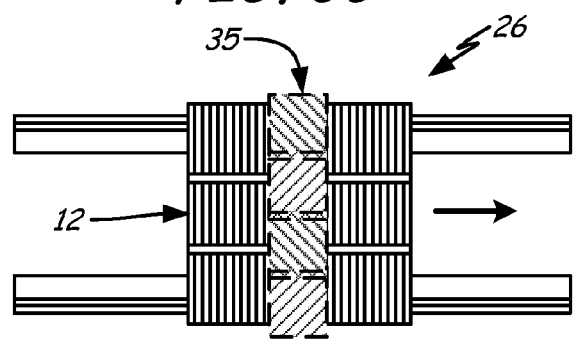

FIGS. 6A-6D show a time sequence of camera array fields of view 31, 33, 34, and 35 acquired with alternating first and second illumination field types. It is understood that solar cell 12 is traveling in the X direction in a nonstop fashion. FIG. 6A shows solar cell 12 at one X location during image acquisition for the entire solar cell 12. Field of view 31 is acquired with a first strobed illumination field type as discussed with respect to FIG. 4. FIG. 6B shows solar cell 12 displaced further in the X direction and field of view 33 acquired with a second strobed illumination field type as discussed with respect to FIG. 5. FIG. 6C shows solar cell 12 displaced further in the X direction and field of view 34 acquired with the first illumination field type and FIG. 6D shows solar cell 12 displaced further in the X direction and field of view 35 acquired with the second illumination field type.

There is a small overlap in the X dimension between field of views 31 and 34 in order to have enough overlapping image information in order to register and digitally merge, or stitch together, the images that were acquired with the first illumination field type. There is also small overlap in the X dimension between field of views 33 and 35 in order to have enough overlapping image information in order to register and digitally merge the images that were acquired with the second illumination field type. In the embodiment with fields of view 30A-30H having extents of 33 mm in the X direction, it has been found that an approximate 5 mm overlap in the X direction between field of views acquired with the same illumination field type is effective. Further, an approximate 15 mm displacement in the X direction between fields of view acquired with different illumination types is preferred.

Images of each feature on solar cell 12 may be acquired with more than two illumination field types by increasing the number of fields of view collected and ensuring sufficient image overlap in order to register and digitally merge, or stitch together, images generated with like illumination field types. Finally, the stitched images generated for each illumination type may be registered with respect to each other. In a preferred embodiment, workpiece transport conveyor 26 has lower positional accuracy than the inspection requirements in order to reduce system cost. For example, encoder 20 may have a resolution of 100 microns and conveyor 26 may have positional accuracy of 0.5 mm or more. Image stitching of fields of view in the X direction compensates for positional errors of the solar cell 12.

It is desirable that each illumination field is spatially uniform and illuminates from consistent angles. It is also desirable for the illumination system to be compact and have high efficiency. Limitations of two prior art illumination systems, linear light sources and ring lights, will be discussed with reference to FIGS. 7-9. Linear light sources have high efficiency, but poor uniformity in the azimuth angle of the projected light. Ring light sources have good uniformity in the azimuth angle of the projected light, but are not compact and have poor efficiency when used with large aspect ratio camera arrays.

Figure 7:
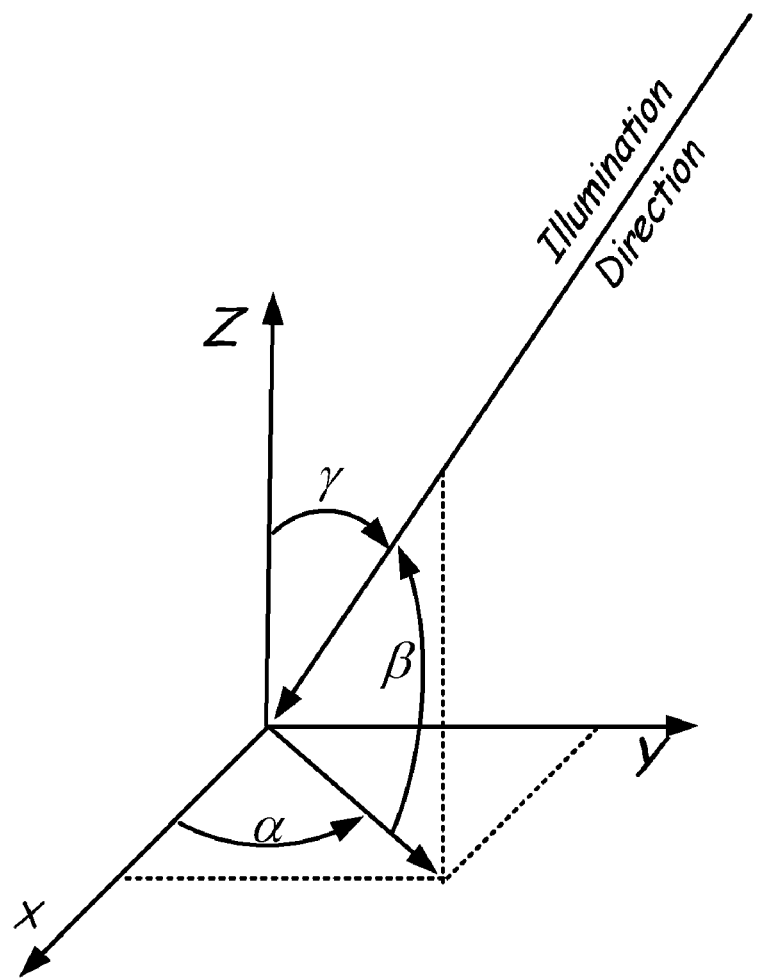
FIG. 7 is a coordinate system for defining illumination direction.

FIG. 7 defines a coordinate system for illumination. Direction Z is normal to solar cell 12 and directions X and Y define horizontal positions on solar cell 12 or other workpiece. Angle $\beta$ defines the elevation angle of the illumination. Angle $\gamma$ redundantly defines the illumination ray angle with respect to normal. Angle $\alpha$ is the azimuth angle of the ray. Illumination from nearly all azimuth and elevation angles is termed cloudy day illumination. Illumination predominantly from low elevation angles, $\beta$, near horizontal is termed dark field illumination. Illumination predominantly from high elevation angles, $\beta$, near vertical is termed bright field illumination. A good, general purpose, illumination system will create a light field with uniform irradiance across the entire field of view (spatial uniformity) and will illuminate from consistent angles across the entire field of view (angle uniformity).

Figure 8:
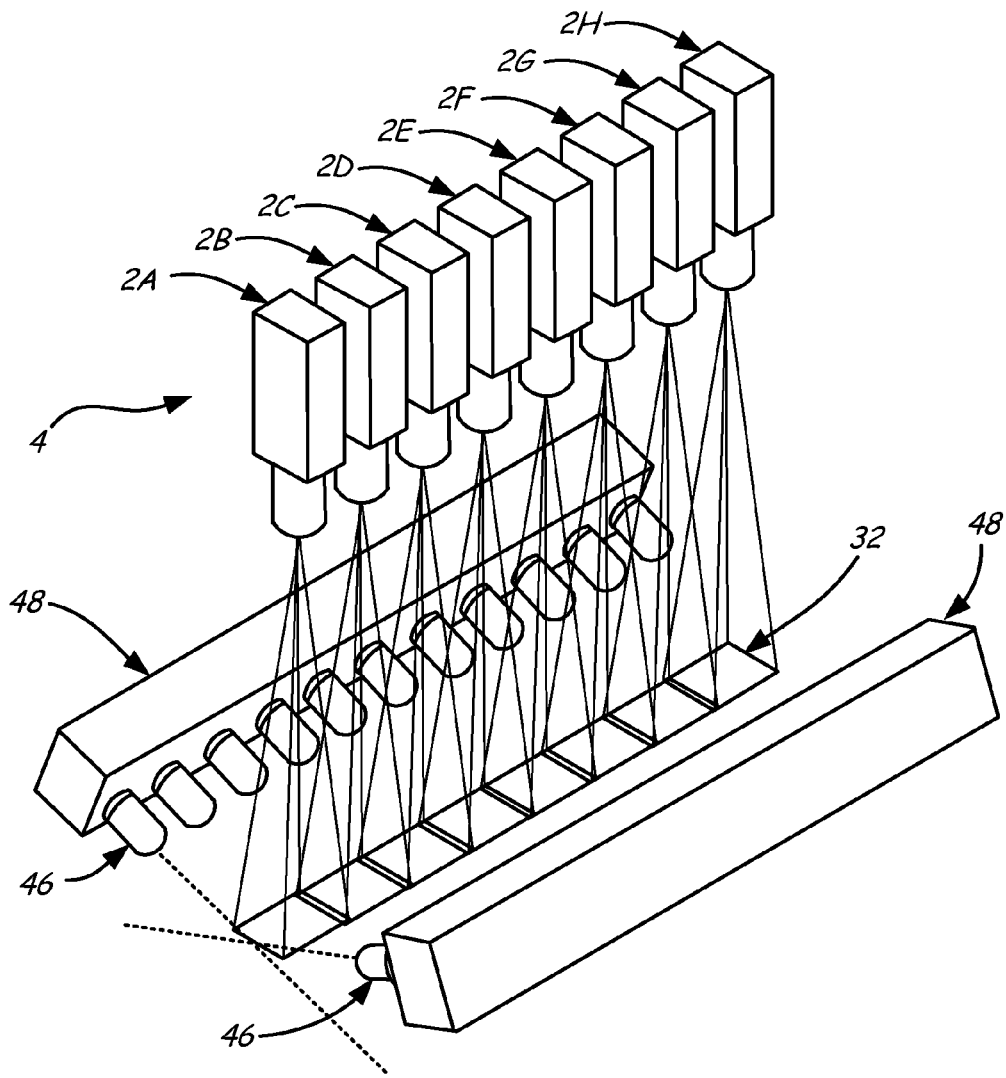
FIG. 8 is a perspective view of a known linear line source illuminating a camera array field of view.

FIG. 8 shows known linear light sources 48 illuminating camera array field of view 32. Linear light source 48 can use an array of LEDs 46 to efficiently concentrate light on a narrow rectangular field of view 32. A disadvantage of using linear light sources 48 is that although the target receives symmetrical illumination from the two directions facing the sources, no light is received from the directions facing the long axis of the FOV.

Figure 9:
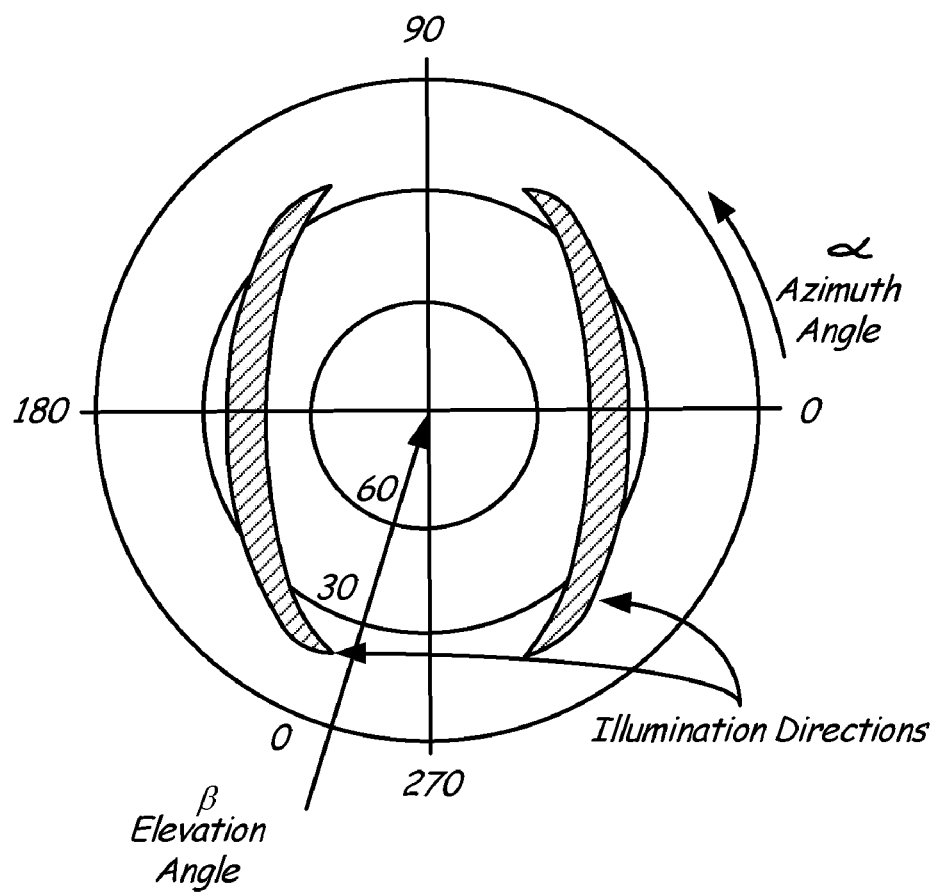
FIG. 9 is a polar plot of the illumination directions of the illuminator shown in FIG. 8.

FIG. 9 is a two axis polar plot showing illumination directions for the two linear light sources 48. The polar plot shows that strong illumination is received by camera array field of view 32 from the direction nearest to light sources 48 (at 0 and 180 degree azimuth angles) and that no illumination received from the 90 and 270 degrees azimuth angle. As the azimuth angle varies between 0 and 90 the source elevation angle drops and the source subtends a smaller angle so less light is received. Camera array field of view 32 receives light which varies in both intensity and elevation angle with azimuth angle. The linear light sources 48 efficiently illuminate field of view 32, but with poor uniformity in azimuth angle. In contrast, known ring lights have good uniformity in azimuth, but must be made large in order to provide acceptable spatial uniformity for large aspect ratio camera field of 32.

Although a ring light could be used to provide acceptable uniformity in azimuth, the ring light would need to be very large to provide acceptable spatial uniformity for camera field of view 32 of approximately 170 mm in the Y direction. For typical inspection applications, it is believed that the ring light would need to be over 500 mm in diameter to provide sufficient spatial uniformity. This enormous ring fails to meet market needs in several respects: the large size consumes valuable space on the assembly line, the large light source is expensive to build, the illumination angles are not consistent across the working field, and it is very inefficient—the light output will be scattered over a significant fraction of the 500 mm circle while only a slim rectangle of the solar cell is actually imaged.

An optical device, referred to as a light pipe, can be used to produce a very uniform light field for illumination. For example, U.S. Pat. No. 1,577,388 describes a light pipe used to back illuminate a film gate. Conventional light pipes, however, need to be physically long to provide uniform illumination.

Figure 10:
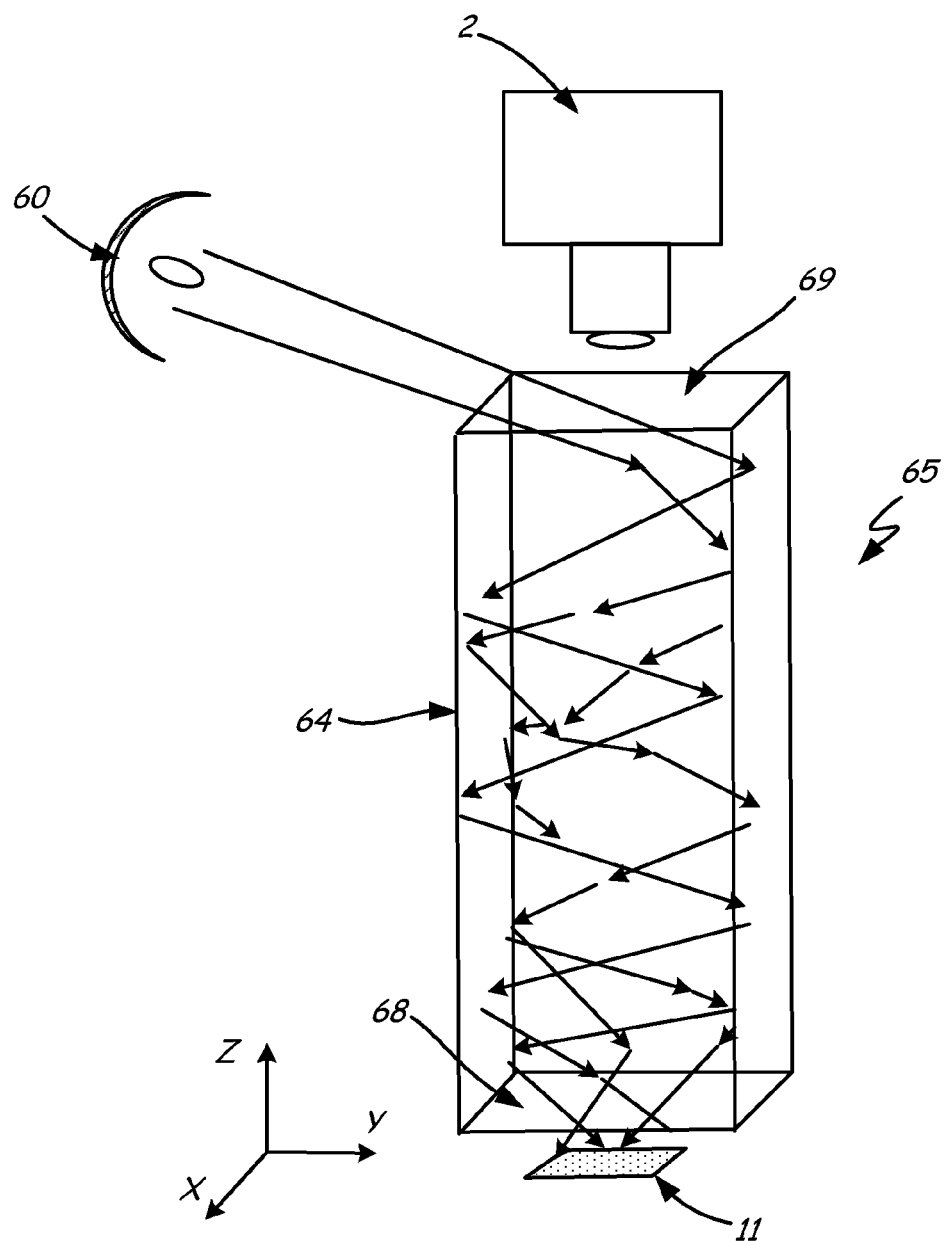
FIG. 10 is a perspective view of an example hollow light pipe illuminator in accordance with an embodiment of the present invention.
Figure 11:
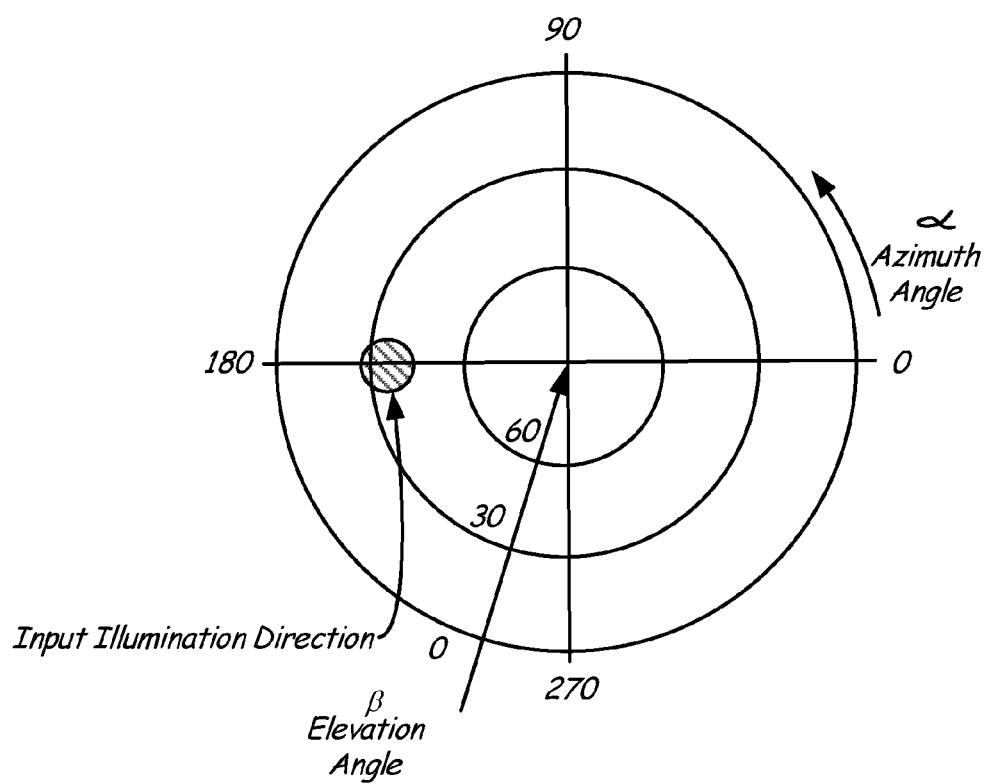
FIG. 11 is a polar plot of the input illumination direction of the illuminator shown in FIG. 10.
Figure 12:
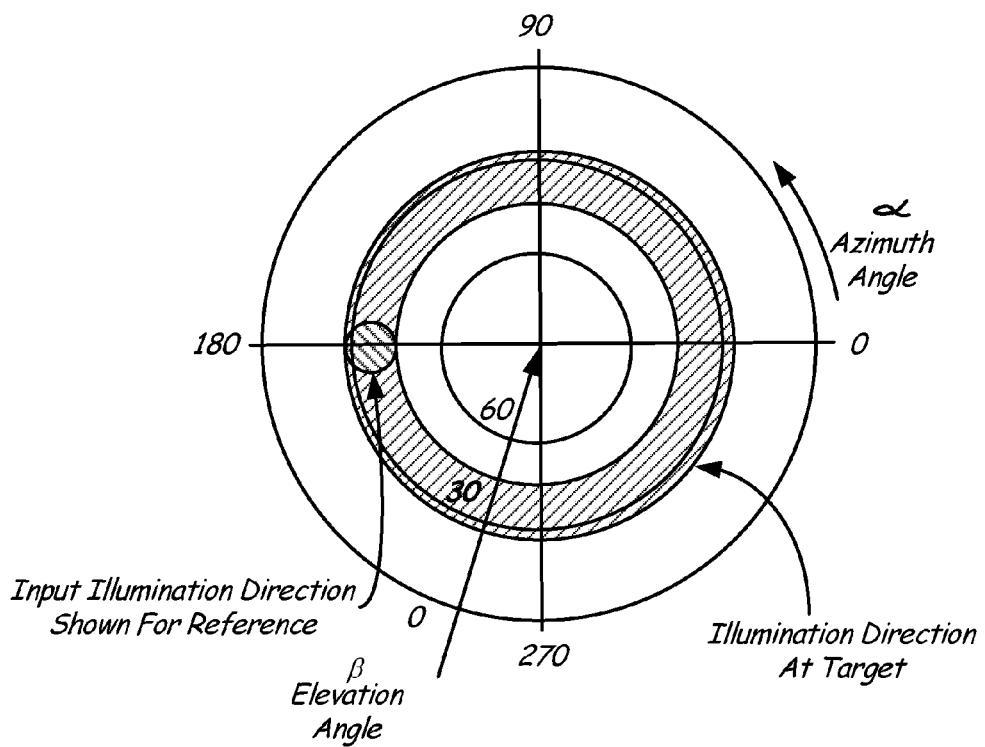
FIG. 12 is a polar plot of the output illumination directions of the illuminator shown in FIG. 10.

A brief description of light pipe principles is provided with respect to FIGS. 10-12. Embodiments of the present invention are then described with respect to FIGS. 13-17 that significantly reduce the length of a light pipe required for uniform illumination. In one embodiment, the interior walls of the light pipe are constructed with reflective materials that scatter light in only one direction. In another embodiment of the present invention, the light pipes are configured with input and output ports that allow simple integration of a camera array to acquire images of a uniformly and efficiently illuminated workpiece.

FIG. 10 shows illuminator 65 which consists of light source 60 and light pipe 64. Hollow box light pipe 64 which, when used as described, will generate a uniform dark field illumination pattern. Camera 2 views workpiece 11 down the length of light pipe 64 through apertures 67 and 69 at the ends of the light pipe. A light source 60, for example an arc in a parabolic reflector, is arranged such that it projects light into the entrance aperture 67 of light pipe 64 with internally reflecting surfaces such that light descends at the desired elevation angle. Alternatively a lensed LED or other source may be used as long as the range of source elevation angles matches the desired range of elevation angles at workpiece 11. The light source may be either strobed or continuous. The fan of rays from light source 60 proceeds across the pipe and downward until it strikes one of the side walls. The ray fan is split and spread in azimuth at the corners of the pipe but the elevation angle is preserved. This expanded ray fan then spreads out, striking many different side wall sections where it is further spread and randomized in azimuth angle and largely unchanged in elevation angle. After a number of reflections all azimuth angles are present at exit aperture 68 and workpiece 11. Therefore all points on the target are illuminated by light from all azimuth angles but only those elevation angles present in the original source. In addition, the illumination field at workpiece 11 is spatially uniform. Note that the lateral extent of light pipe 64 is only slightly larger than the field of view in contrast to the required size of a ring light for the condition of spatially uniform illumination.

FIG. 11 shows the polar plot of the illumination direction at the source, a nearly collimated bundle of rays from a small range of elevation and azimuth angles.

FIG. 12 is a polar plot of the rays at workpiece 11 and the angular spread of the source is included for comparison. All azimuth angles are present at workpiece 11 and the elevation angles of the source are preserved.

As the elevation angle of light exiting illuminator 65 is the same as those present in the source 60, it is relatively easy to tune those angles to specific applications. If a lower elevation illumination angle is desired then the source may be aimed closer to the horizon. The lower limit to the illumination angle is set by the standoff of the light pipe bottom edge as light cannot reach the target from angles below the bottom edge of the light pipe. The upper limit to the illumination elevation angle is set by the length of light pipe 66 since several reflections are required to randomize, or homogenize, the illumination azimuth angle. As elevation angle is increased there will be fewer bounces for a given length light pipe 64 before reaching workpiece 11.

The polygonal light pipe homogenizer only forms new azimuth angles at its corners, therefore many reflections are needed to get a uniform output If all portions of the light pipe side walls could spread or randomize the light pattern in the azimuth direction, then fewer reflections would be required and the length of the light pipe in the Z direction could be reduced making the illuminator shorter and/or wider in the Y direction.

Figure 13:
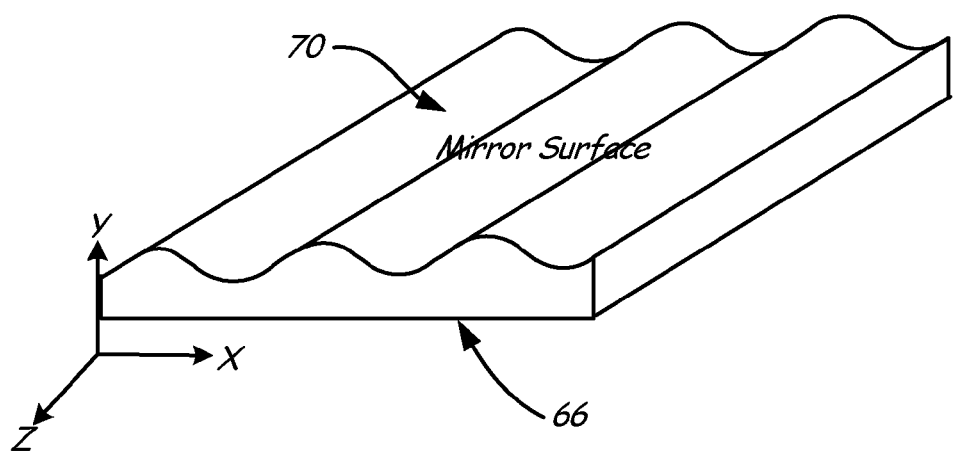
FIG. 13 is a perspective view of a reflective surface of a light pipe wall in accordance with an embodiment of the present invention.
Figures 14A, 14B:
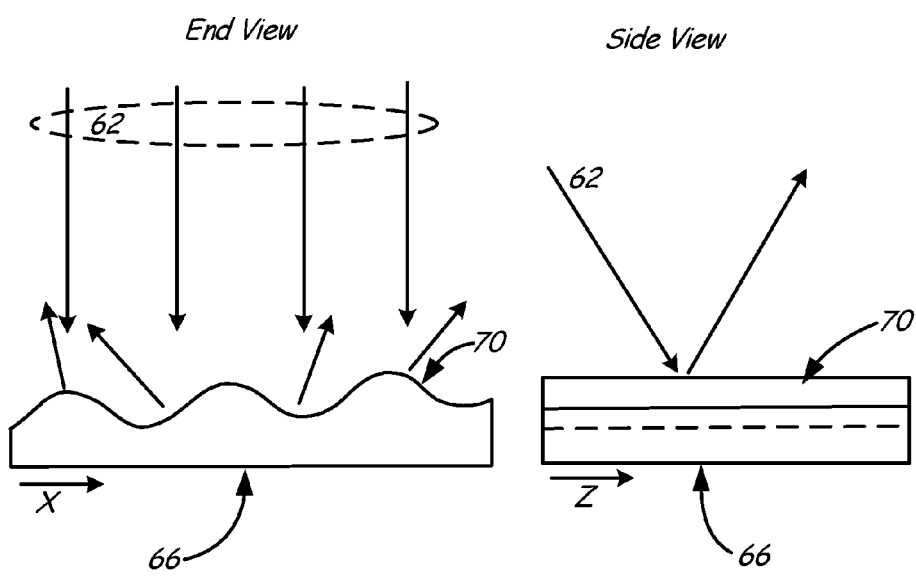
FIGS. 14A-B are cross sectional views of the reflective surface shown in FIG. 13

FIGS. 13 and 14 illustrate an embodiment of the present invention with light pipe side walls which diffuse or scatter light in only one axis. In this embodiment it is preferred that the azimuth angles of the light bundle be spread on each reflection while maintaining elevation angles. This is achieved by adding curved or faceted, reflective surface 70 to the interior surface of light pipe side wall 66 as shown in FIG. 13. Cross sectional views of side wall 66 are shown in FIGS. 14A and 14B. FIG. 14A demonstrates how a collimated light ray bundle 62 is spread perpendicular to the axis of the cylindrical curvature on reflective surface 70. In FIG. 14B, the angle of reflection for light ray bundle 62 is maintained along the axis of the cylindrical curvature on reflective surface 70. Hence, the elevation angle of the source is maintained since the surface normal at every point of reflector 70 has no Z component. The curved, or faceted, surface of reflective surface 70 creates a range of new azimuth angles on every reflection over the entire surface of the light pipe wall 66 and therefore the azimuth angle of the source is rapidly randomized. Embodiment of the present invention can be practiced using any combination of refractive, diffractive and reflective surfaces for the interior surface of light pipe side wall 66.

In one aspect, reflective surface 70 is curved in segments of a cylinder. This spreads incoming light evenly in one axis, approximating a one-dimensional Lambertian surface, but does not spread light in the other axis. This shape is also easy to form in sheet metal. In another aspect, reflective surface 70 has a sine wave shape. However, since a sine wave shape has more curvature at the peaks and valleys and less curvature on the sides, the angular spread of light bundle 62 is stronger at the peaks and valleys than on the sides.

Figure 15A:
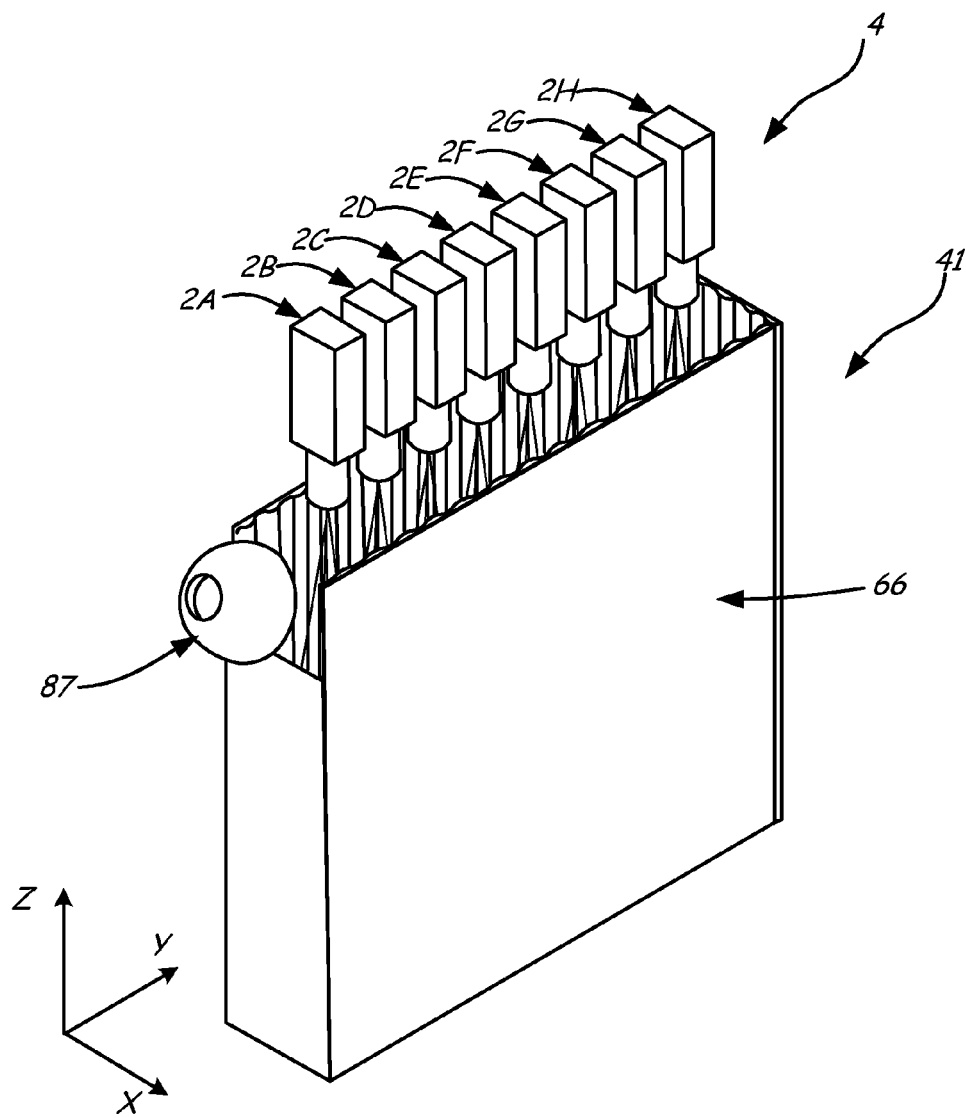
FIG. 15A is a perspective view of a light pipe illuminator and camera array in accordance with an embodiment of the present invention.
Figure 15B:
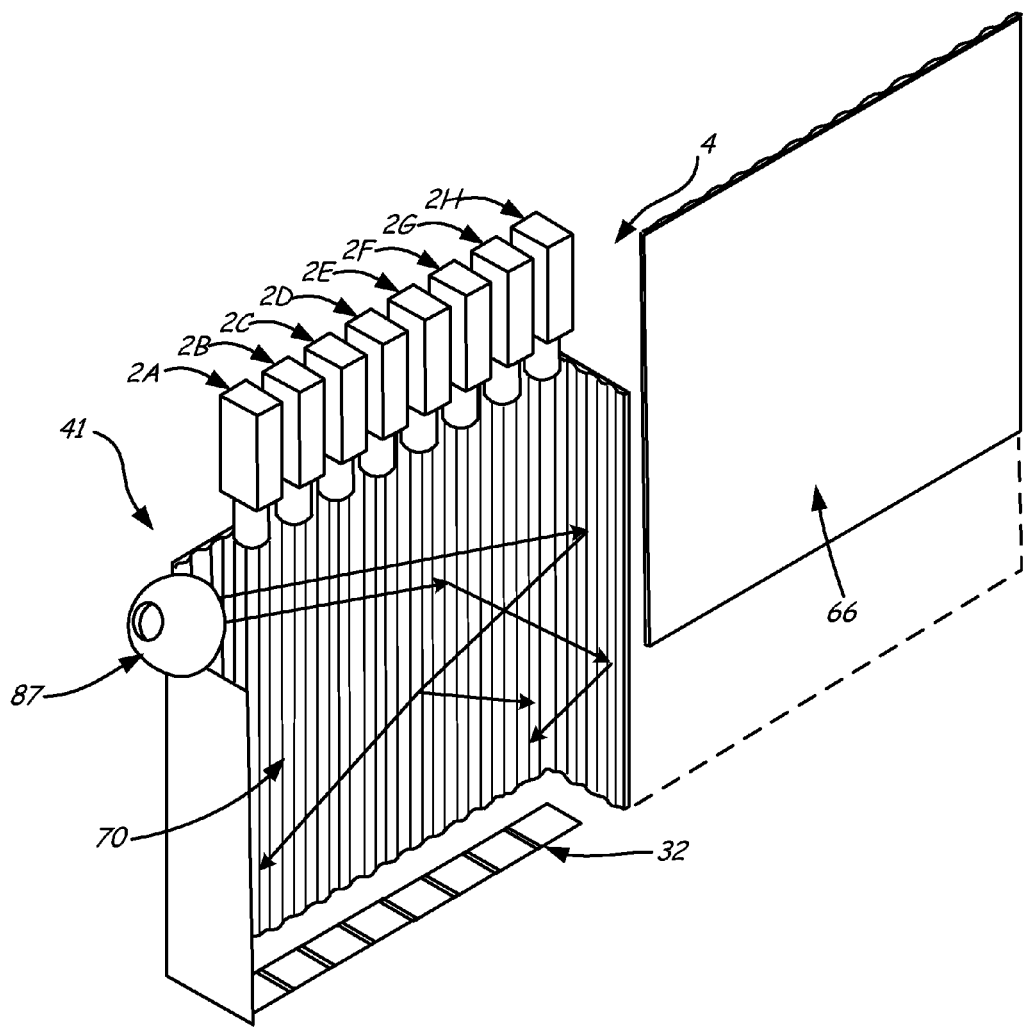
FIG. 15B is a cutaway perspective view of a light pipe illuminator and camera array in accordance with an embodiment of the present invention.
Figure 16:
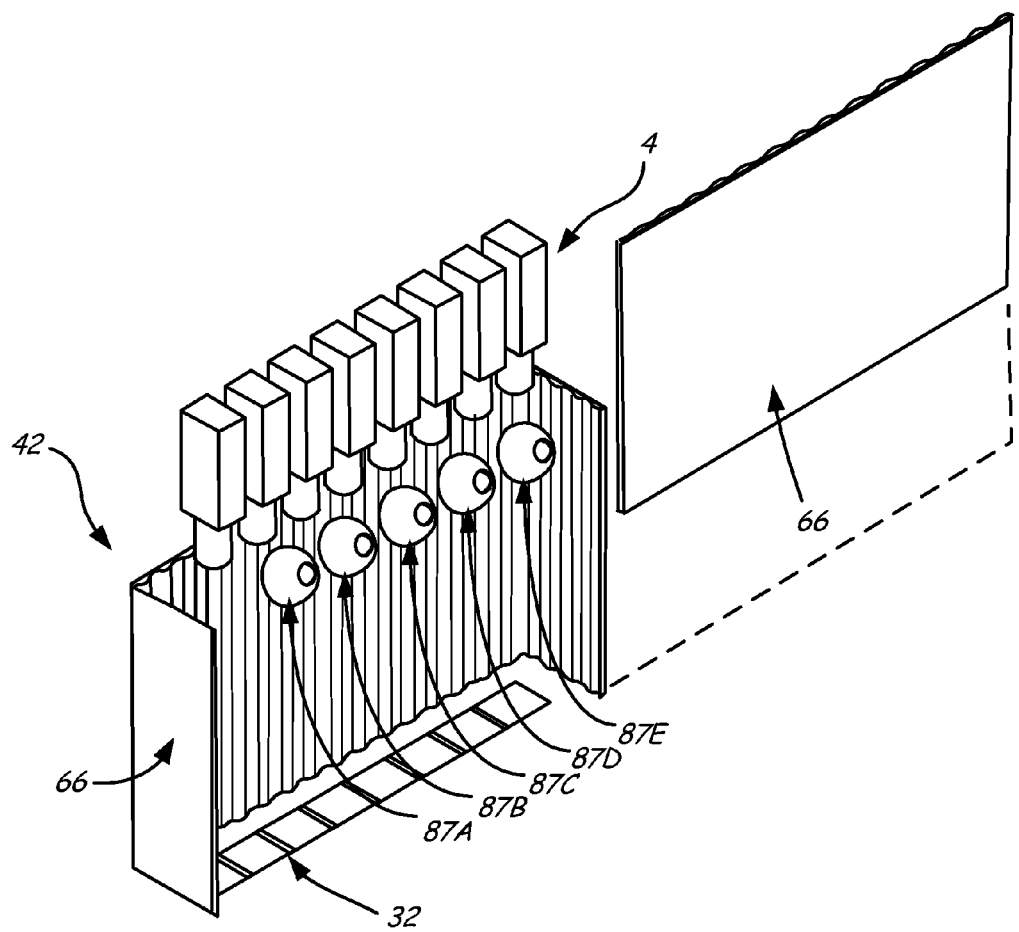
FIG. 16 is a cutaway perspective view of a camera array and illuminator with multiple sources in accordance with an embodiment of the present invention.

FIGS. 15A and 15B show the curved, reflective surfaces applied to the interior surfaces of light pipe illuminator 41 for camera array 4. Light pipe illuminator includes side walls 66 and light source 87. The one-dimensional diffusely reflecting surfaces 70 randomize azimuth angles more rapidly than a light pipe constructed of planar, reflective interior surfaces. This allows a more compact light pipe to be used which allows camera array 4 to be closer to the workpiece. FIG. 15B shows how light rays are randomized in azimuth angle after a small number of reflections.

Light pipe illuminator 42 can be shortened in the Z direction compared to illuminator 41 if multiple light sources are used. Multiple sources, for example a row of collimated LEDs, reduce the total number of reflections required to achieve a spatially uniform source and hence reduce the required light pipe length. Illuminator 42 is illustrated with light sources 87A-87E which may also be strobed arc lamp sources.

Figure 17A:
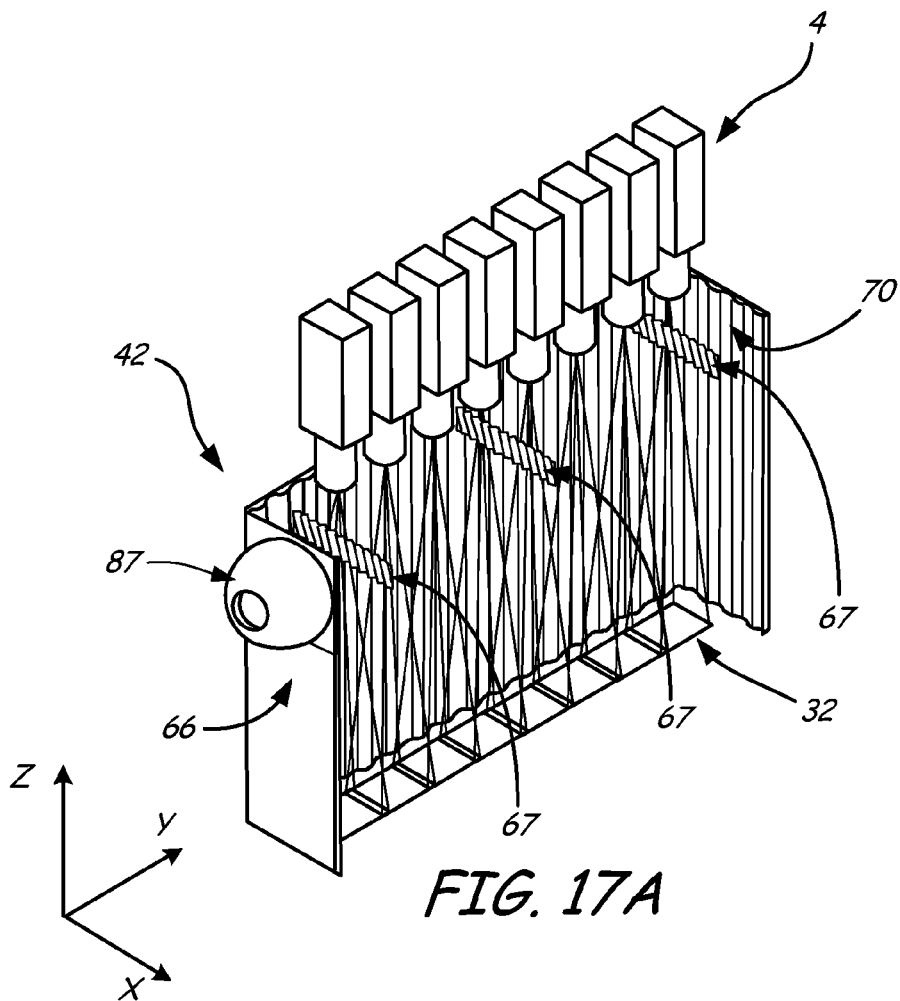
FIG. 17A is a perspective cutaway view of an illuminator and camera array in accordance with an embodiment of the present invention.
Figure 17B:
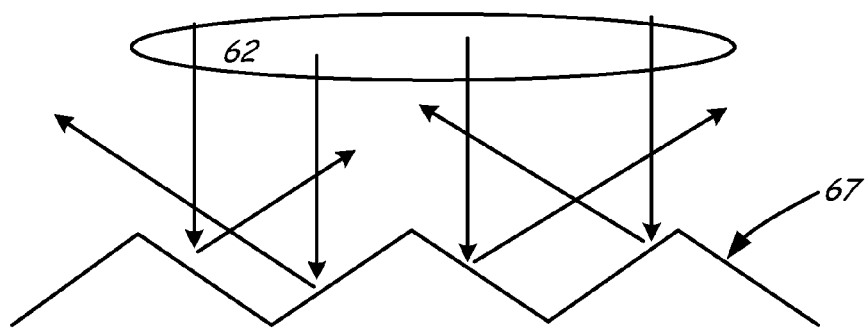
FIG. 17B is a cross sectional view of a chevron shaped mirror employed in accordance with an embodiment of the present invention.

In another aspect of the present invention shown in FIGS. 17A-17B, illuminator 43 includes mirrors 67 that reflect portions of the input beam from source 87 to the desired source elevation angle. Like the multiple source embodiment, this also results in a spatially uniform light field in a shorter light pipe. Mirrors 67 are placed between cameras to avoid blocking the view of the target and at different heights so that each mirror intercepts a portion of the light coming from source 67. Mirrors are shaped to reflect light at the desired elevation angle and toward light pipe side walls 66 where the curved, reflected surfaces 70 rapidly randomize the source azimuth direction. A cross sectional view of mirror 67 is shown in FIG. 17B. Mirror 67 may be, for example, a flat mirror that is formed into a series of chevrons.

Figure 18:
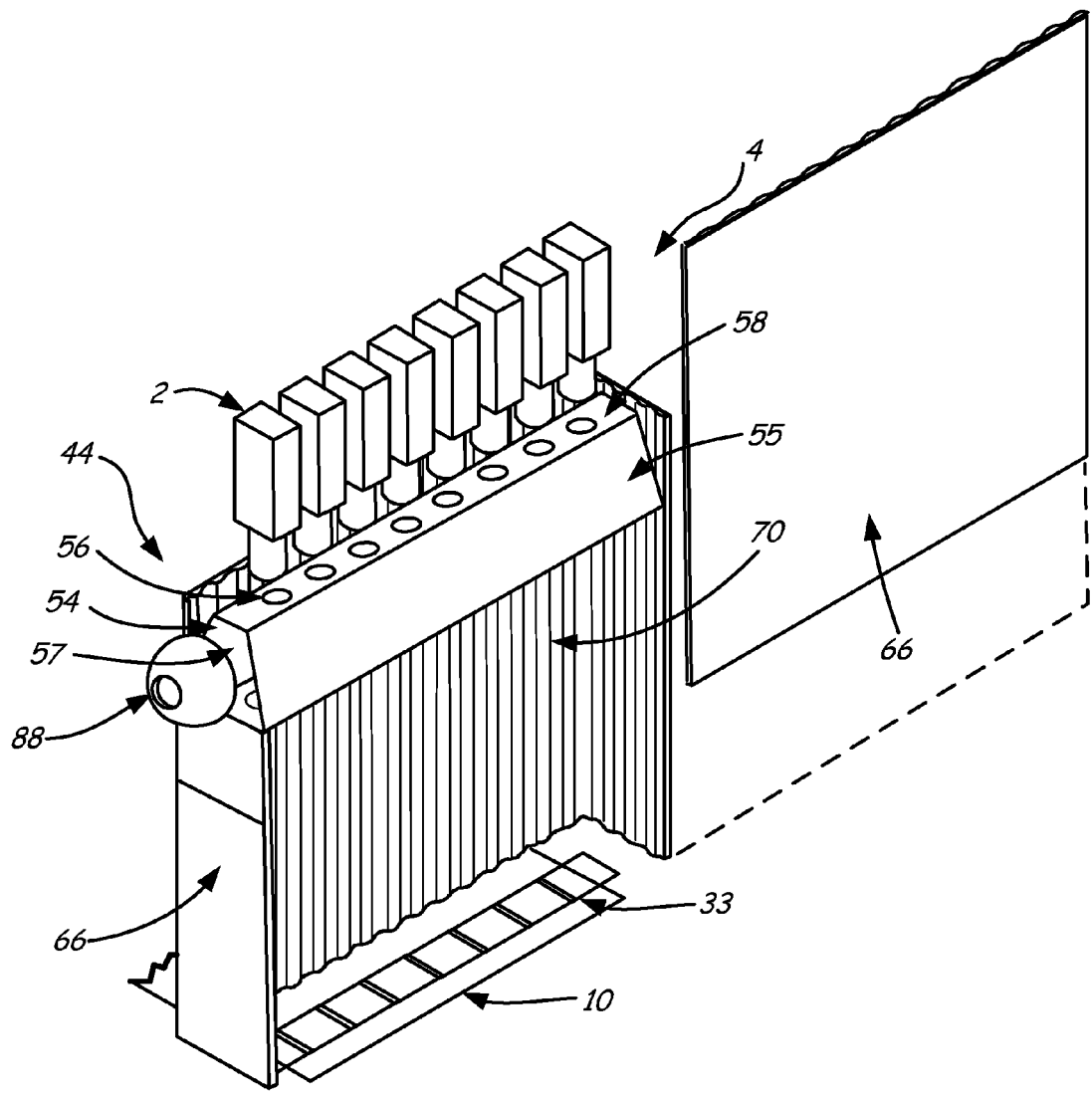
FIG. 18 is a cutaway perspective view of an illuminator and camera array in accordance with an embodiment of the present invention.
Figure 19:
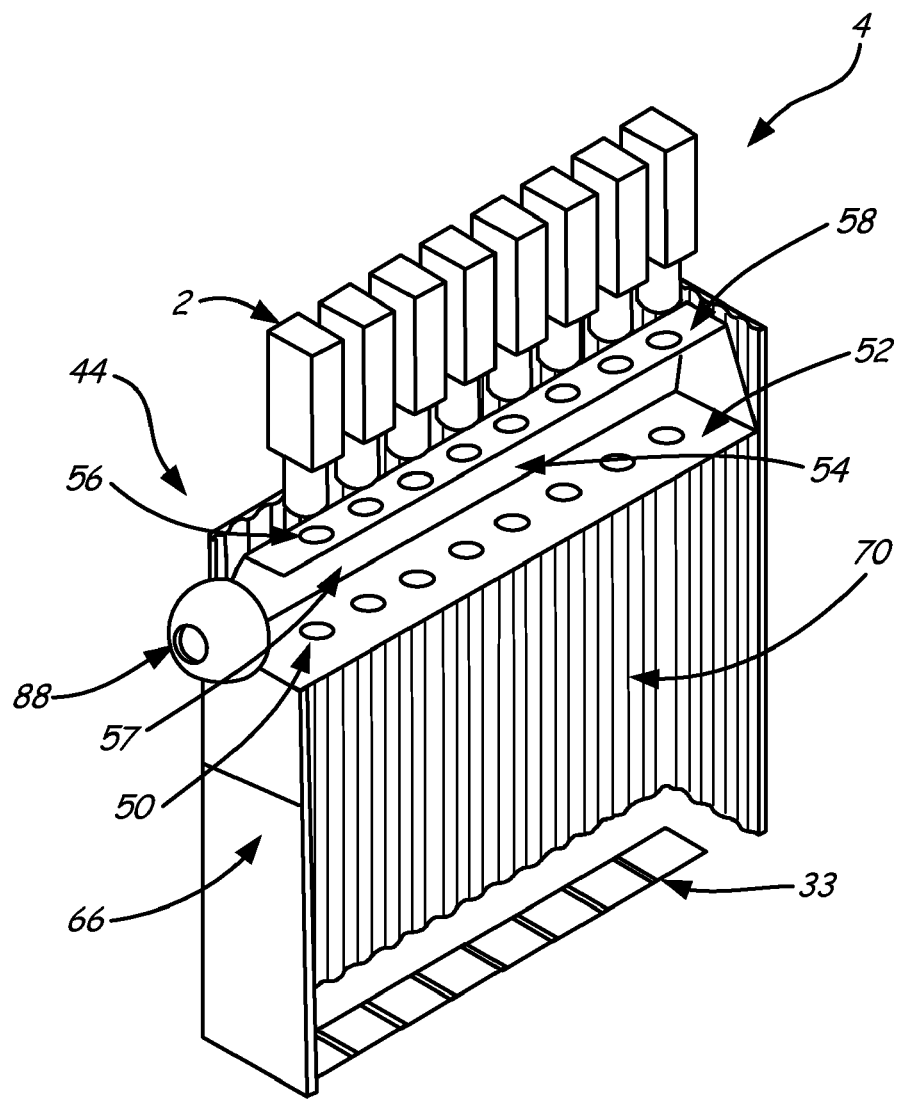
FIG. 19 is a second cutaway perspective view of the illuminator and camera array shown in FIG. 18.

In another embodiment of the present invention, FIGS. 18 and 19 illustrate illuminator 44 integrated with camera array 4. Light is injected by source 88 into light mixing chamber 57 defined by mirrors 54 and 55, top aperture plate 58, and diffuser plate 52. The interior surfaces of 54, 55, and 58 are reflective, whereas diffuser plate 52 is preferably constructed of a translucent, light diffusing material. Apertures 56 are provided on top plate 58 and apertures 50 are provided on diffuser plate 52 such that cameras 2 have an unobstructed view of the workpiece. In order to more clearly visualize diffuser plate 52 and apertures 50, mirror 55 has been removed in FIG. 19, compared with FIG. 18.

Figure 20:
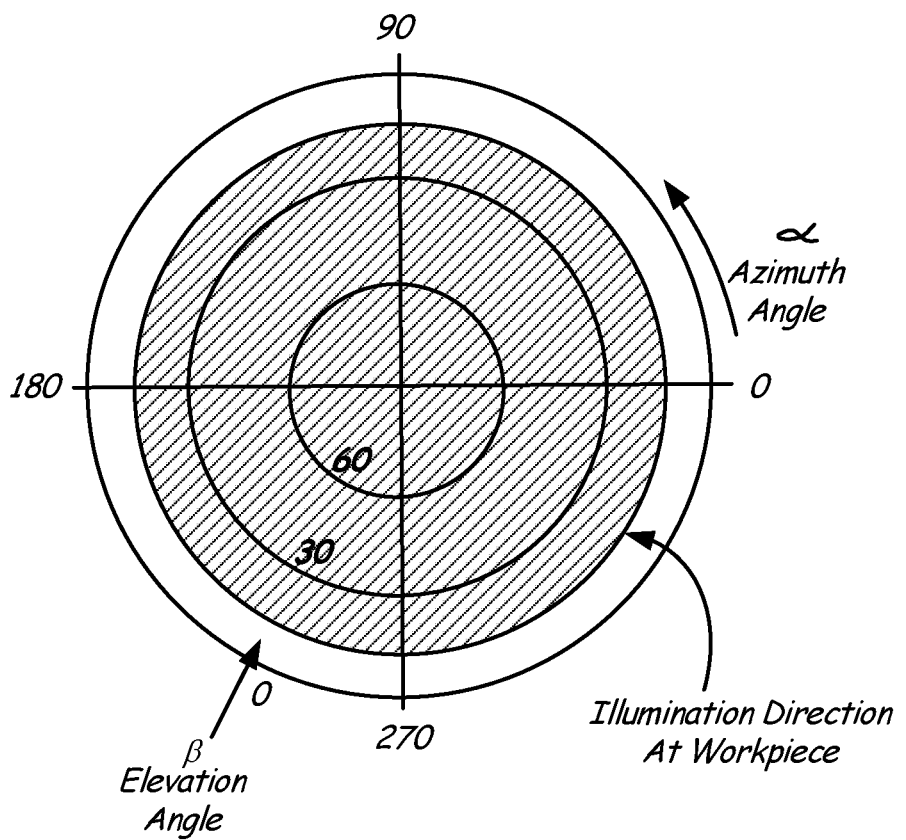
FIG. 20 is a polar plot of the illumination directions of the illuminator shown in FIGS. 18 and 19.

Light projected by source 88 is reflected by mirrors 54 and 55 and aperture plate 58. As the light reflects in mixing chamber 57, diffuser plate also reflects a portion of this light and is injected back into mixing chamber 57. After multiple light reflections within mixing chamber 57, diffuser plate 52 is uniformly illuminated. The light transmitted through diffuser plate 52 is emitted into the lower section of illuminator 44 which is constructed of reflective surfaces 70, such as those discussed with reference to FIGS. 13 and 14. Reflective surfaces 70 preserve the illumination elevation angle emitted by diffuser plate 52. The result is a spatially uniform illumination field at workpiece 12. FIG. 20 is a polar plot showing the output illumination directions of illuminator 44. Illuminator 44 creates an output light field, as shown in FIG. 20, which is termed cloudy day since illumination is nearly equal from almost all elevation and azimuth angles. The range of output elevation angles, however, can be controlled by the diffusing properties of diffuser plate 52.

Figure 21:
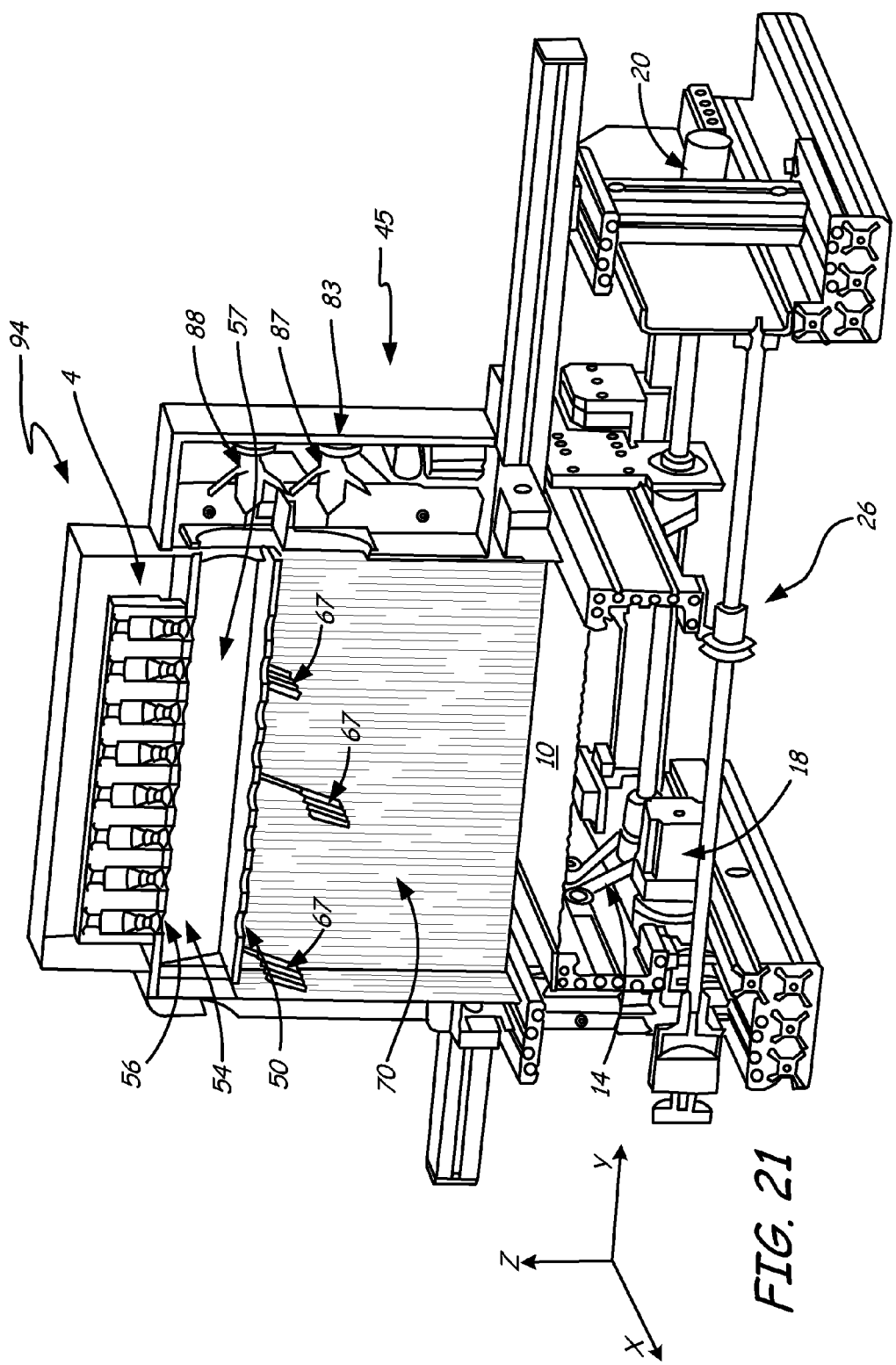
FIG. 21 is a cross-sectional perspective view of an inspection sensor in accordance with an embodiment of the present invention.
Figure 22:
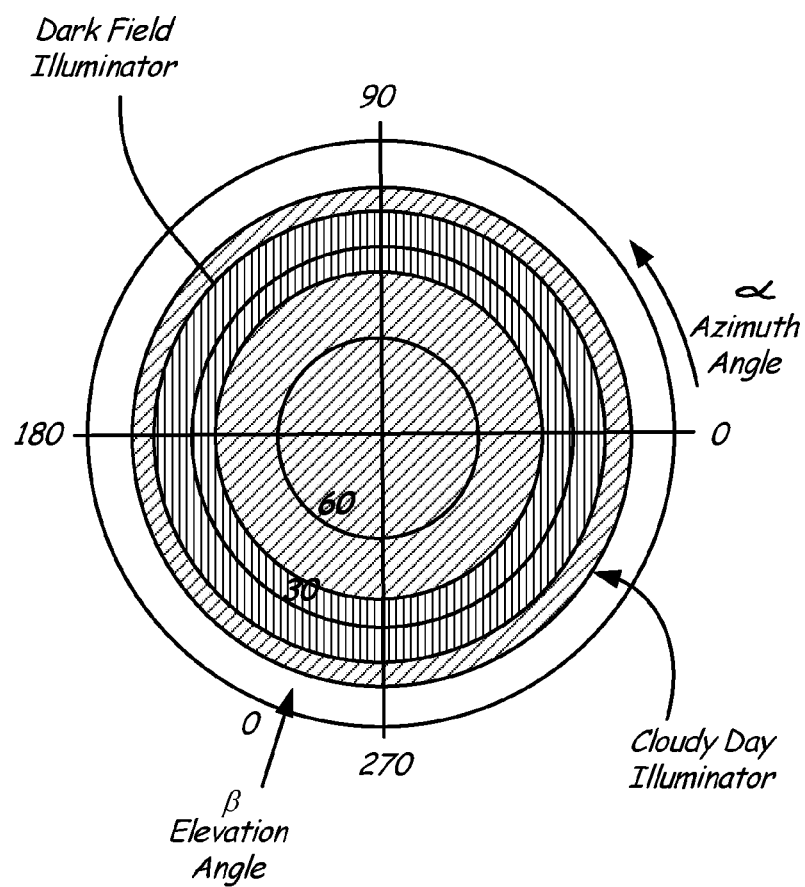
FIG. 22 is a polar plot of the illumination directions of the illuminator shown in FIG. 21.

FIG. 21 shows another embodiment of optical inspection sensor 94. Optical inspection sensor 94 includes camera array 4 and integrated illuminator 45. Illuminator 45 facilitates independently controlled cloudy day and dark field illumination. A dark field illumination field is produced on solar cell 12 by energizing light source 87. A cloudy day illumination field is projected onto solar cell 12 by energizing light source 88. FIG. 22 shows the polar plot and illumination directions for the cloudy day and dark field illuminations. In one aspect, sources 87 and 88 are strobed to suppress motion blurring effects due to the transport of solar cell 12 in a non-stop manner.

It is understood by those skilled in the art that the image contrast of various object features vary depending on several factors including the feature geometry, color, reflectance properties, and the angular spectrum of illumination incident on each feature. Since each camera array field of view may contain a wide variety of features with different illumination requirements, embodiments of the present invention address this challenge by imaging each feature and location on workpiece 12 two or more times, with each of these images captured under different illumination conditions and then stored into a digital memory. In general, the inspection performance may be improved by using object feature data from two or more images acquired with different illumination field types.

It should be understood that embodiments of the present invention are not limited to two lighting types such as dark field and cloudy day illumination field nor are they limited to the specific illuminator configurations. The light sources may project directly onto workpiece 12. The light sources may also have different wavelengths, or colors, and be located at different angles with respect to workpiece 12. The light sources may be positioned at various azimuthal angles around workpiece 12 to provide illumination from different quadrants. The light sources may be a multitude of high power LEDs that emit light pulses with enough energy to "freeze" the motion of workpiece 12 and suppress motion blurring in the images. Numerous other lighting configurations are within the scope of the invention including light sources that generate bright field illumination fields or transmit through the substrate of workpiece 12 to backlight features to be inspected. For example, since silicon is semi-transparent at near infrared wavelengths, it is especially effective to backlight solar cell 12 with strobed, near infrared light to inspect for microcracks and holes in the substrate.

Several solar cell inspection requirements necessitate the need to capture three dimensional image data at full production rates. These requirements include measuring metallization print height and wafer bowing. Three dimensional information such as the profile of a collector finger may be measured using well known laser triangulation, phase profilometry, or moiré methods, for example. U.S. Pat. No. 6,577,405 (Kranz, et al) assigned to the assignee of the present invention describes a representative three dimensional imaging system. Stereo vision based systems are also capable of generating high speed three dimensional image data.

Stereo vision systems are well known. Commercial stereo systems date to the stereoscopes of the $19^{th}$ century. More recently a great deal of work has been done on the use of computers to evaluate two camera stereo image pairs ("A Taxonomy and Evaluation of Dense Two-Frame Stereo Correspondence Algorithms" by Scharstein and Szeliski) or multiple cameras ("A Space-Sweep Approach to True Multi-Image Matching" by Robert T. Collins). This last reference includes mention of a single camera moved relative to the target for aerial reconnaissance.

An alternative stereo vision system projects a structured light pattern onto the target, or workpiece, in order to create unambiguous texture in the reflected light pattern ("A Multibaseline Stereo System with Active Illumination and Real-time Image Acquisition" by Sing Bing Kang, Jon A. Webb, C. Lawrence Zitnick, and Takeo Kanade).

To acquire high speed two and three dimensional image data to meet solar cell inspection requirements, multiple camera arrays may be arranged in a stereo configuration with overlapping camera array fields of view. The solar cell can then be moved in a nonstop fashion with respect to the camera arrays. Multiple, strobed illumination fields effectively "freeze" the image of the solar cell to suppress motion blurring.

Figure 23:
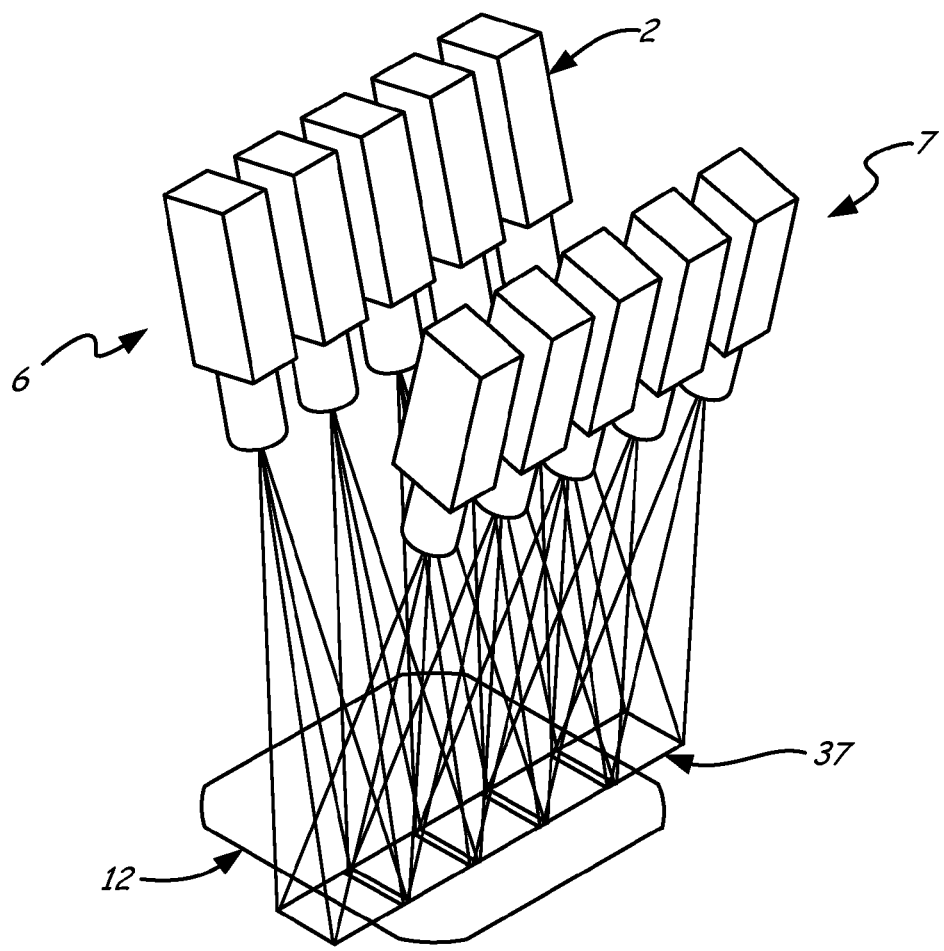
FIG. 23 is a perspective view of two camera arrays arranged in a stereo configuration in accordance with an embodiment of the present invention.

FIG. 23 shows camera arrays 6 and 7 arranged in a stereo configuration. Camera arrays 6 and 7 image solar cell 12 with overlapping camera array fields of view 37. The illumination system is removed for clarity.

Figure 24:
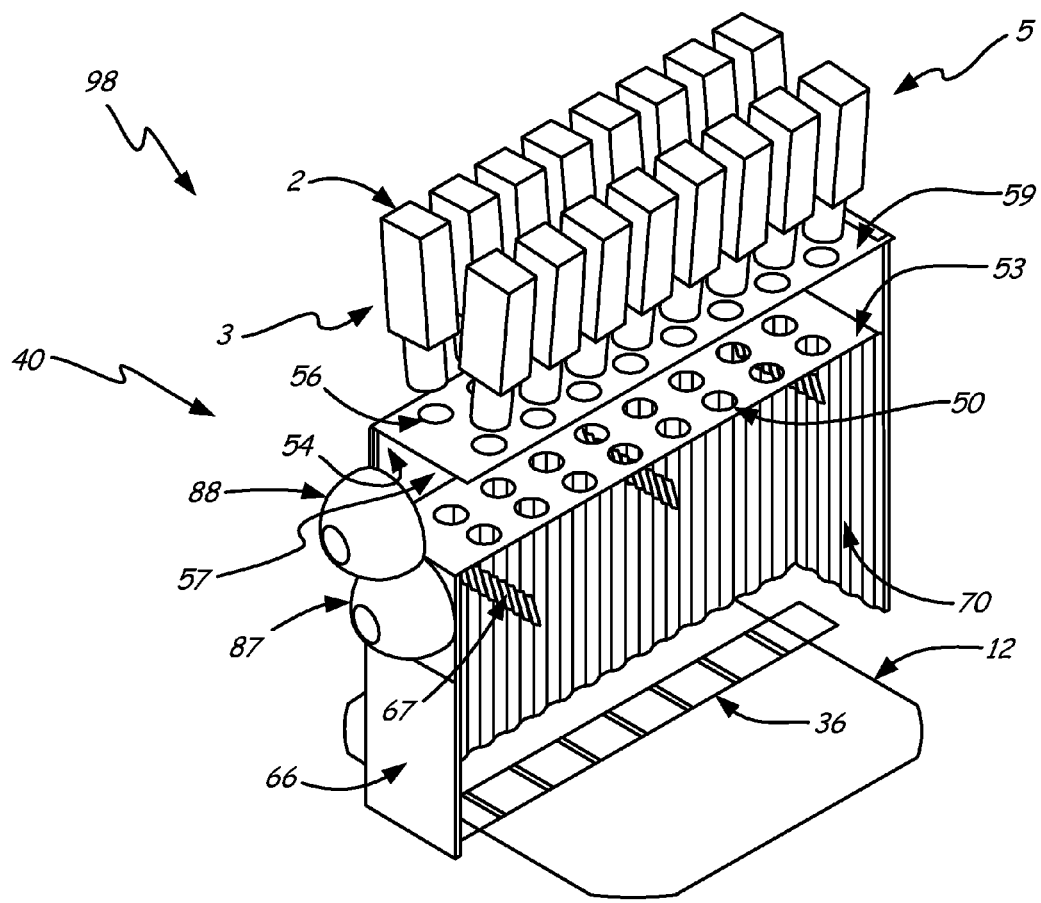
FIG. 24 is a cutaway perspective view of two camera arrays arranged in a stereo configuration with an integrated illuminator in accordance with an embodiment of the present invention.

FIG. 24 is a cutaway perspective view of optical inspection sensor 98 with integrated illuminator 40 for high speed acquisition of stereo image data. Camera arrays 3 and 5 are arranged in a stereo configuration with overlapping fields of view 36 on solar cell 12. Solar cell 12 moves in a nonstop fashion relative to inspection sensor 98. Top aperture plate 59 includes apertures 56 and translucent diffuser plate 53 includes apertures 50 to allow unobstructed views of field of view 36 for camera arrays 3 and 5. Energizing light source 88 will create a cloudy day illumination field type on solar cell 12 and energizing light source 87 will create a darkfield illumination field type. Other illumination field types, such as backlight, may be accomplished by suitable arrangement of a strobed illuminator such that light transmitted through, or past the edges, of solar cell 12 are captured by camera arrays 3 and 5. The image acquisition sequence may be, for example, a series of overlapped images captured simultaneously by both camera arrays 3 and 5 with alternating strobed cloudy day, darkfield, and backlight illumination field types.

Referring back to block diagram FIG. 3, the functional block diagram of optical inspection sensor 98 is very similar to the block diagram of optical inspection sensor 94. For optical inspection sensor 98, however, camera array 4 is removed and replaced by camera arrays 3 and 5 which are in turn interfaced to main electronics board 80. Image memory 82 preferably contains enough capacity to store all images generated by camera arrays 3 and 5 for one solar cell 12. Image data is read out of image memory 82 and transferred to system computer 76 over a high speed electrical interface such as PCI Express (PCIe).

Application inspection program 71 computes three dimensional image data by known stereo methods using the disparity or offset of image features between the image data from camera arrays 3 and 5. Inspection results are computed by application program 71 for solar wafer 12 properties and defects such as wafer geometry, chipped edges, holes, cracks, microcracks, surface inspection, bow, saw marks, and color. Print inspection results for position, thickness, width, length, and interruptions may also be computed by application program 71. The registration of the metalized print may also be enhanced by measuring fiducials, such as those that are laser etched onto the surface of solar cell 12. These fiducials often show good contrast in darkfield illuminated images and may be used to establish a coordinate system for measuring registration. A combination of two and/or three dimensional image data may be used for any of these inspection computations.

Figure 25:
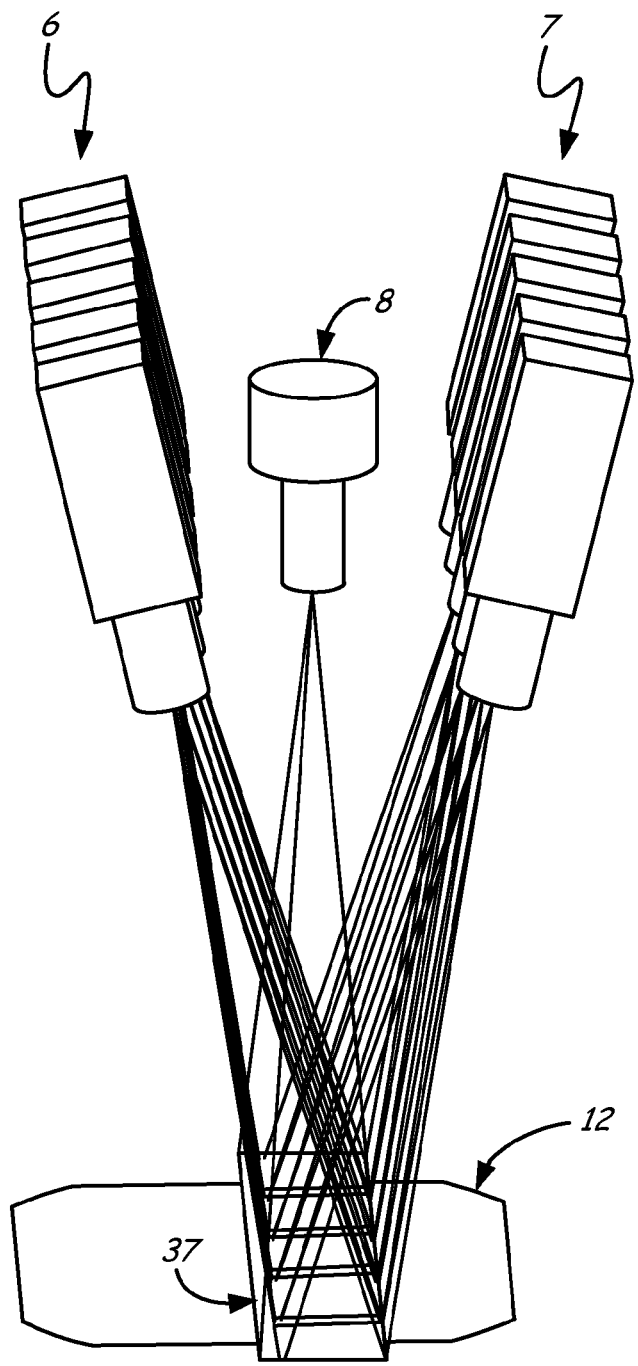
FIG. 25 is a perspective view of two camera arrays and a structured light projector arranged in accordance with an embodiment of the present invention.

FIG. 25 shows another embodiment where camera arrays 6 an 7 are arranged in a stereo configuration with overlapping camera array fields of view 37 on solar cell 12. The integrated cloudy day and darkfield illuminator has been removed for clarity. Stereo vision systems sometimes fail in the absence of observable structure on the object. A method of overcoming this is to add artificial structure or "texture" to the surface with a patterned light source that can then be viewed by cameras arranged in a stereo configuration. Structured light projector 8 projects a strobed light pattern onto solar cell 12 over the camera array field of view 37. The light pattern may be, for example, a laser stripe, a series of laser stripes, or a random dot pattern. The disparity of the projected pattern as viewed by camera arrays 6 and 7 may be used by application program 71 to compute three dimensional image data. The image acquisition sequence may be a series of overlapped images captured simultaneously by both camera arrays 6 and 7 with alternating strobed cloudy day, darkfield, and structured light pattern illumination field types.

Figure 26:
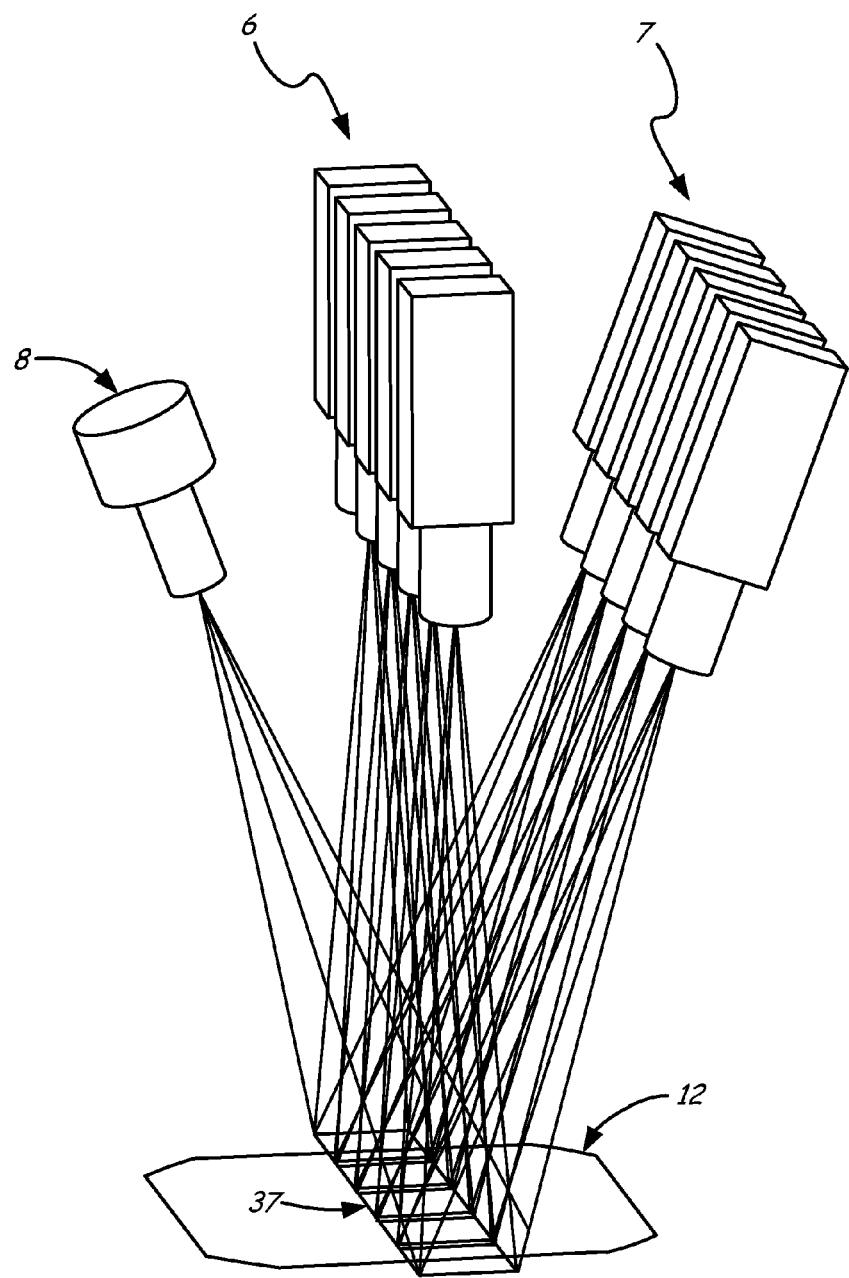
FIG. 26 is a perspective view of two camera arrays and a structured light projector arranged in accordance with an embodiment of the present invention.

FIG. 26 shows another embodiment with camera arrays 6 and 7 arranged in a stereo configuration and with structured light projector 8. The integrated cloudy day and darkfield illuminator has been removed for clarity. Camera array 6 is arranged to view solar cell 12 from a vertical direction to eliminate the perspective view, as in FIG. 25, to improve two dimensional measurement of solar cell 12 features.

Figure 27:
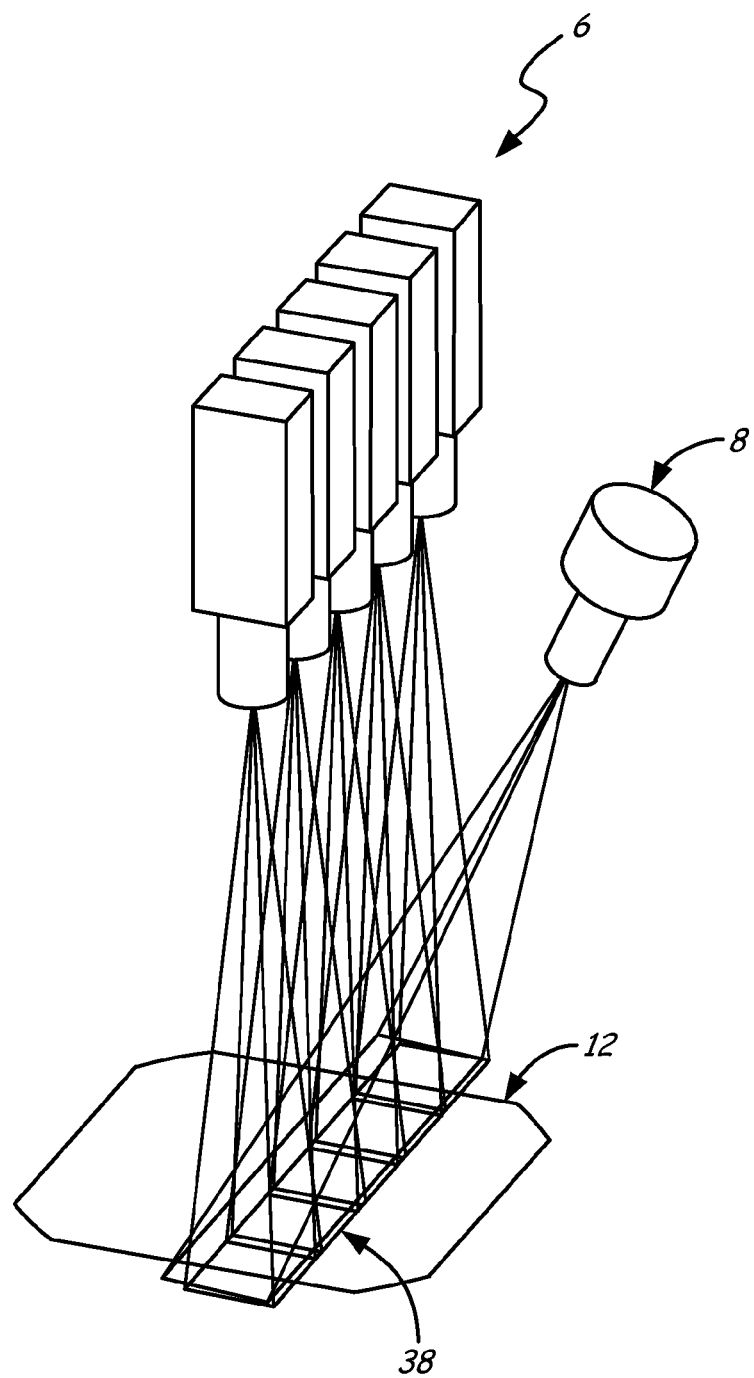
FIG. 27 is a perspective view of a camera array and structured light projector in accordance with an embodiment of the present invention.

FIG. 27 shows another embodiment with camera array 6 arranged to view camera array field of view 38 on solar cell 12. Structured light projector 8 projects a strobed light pattern onto solar cell 12 over the camera array field of view 38. The light pattern may be, for example, a laser stripe, a series of laser stripes, a sinusoidal pattern, or a random dot pattern. Range to solar cell 12 and its features are calculated by known methods by measuring the position of the projected light pattern as observed by camera array 6. Optional cloudy day, darkfield, brightfield, backlight, or other light sources have not been shown for clarity.

Although the present invention has been described with reference to preferred embodiments, workers skilled in the art will recognize that changes may be made in form and detail without departing from the spirit and scope of the invention.

What is claimed is:
1. An optical inspection system comprising:
a workpiece transport configured to transport the workpiece in a nonstop manner; and
an illuminator configured to provide a first strobed illumination field type and a second strobed illumination field type, the illuminator including a light pipe having a first end proximate the workpiece, and a second end opposite the first end and spaced from the first end, the light pipe also having at least one reflective sidewall, and wherein the first end has an exit aperture and the second end has at least one second end aperture to provide a view of the workpiece therethrough;
a first array of cameras configured to digitally image the workpiece, wherein the first array of cameras is configured to generate a first plurality of images of the workpiece with the first illumination field and a second plurality of images of the workpiece with the second illumination field;
a second array of cameras configured to digitally image the workpiece, wherein the second array of cameras is configured to generate a third plurality of images of the workpiece with the first illumination field and a fourth plurality of images of the workpiece with the second illumination field;
wherein the first and second arrays of cameras are configured to provide stereoscopic imaging of the workpiece; and
a processing device operably coupled to the illuminator and the first and second arrays of cameras, the process- ing device being configured to provide at least some of the first, second, third, and fourth pluralities of images to an other device.

2. The optical inspection system of claim 1, wherein the first array of cameras includes non-telecentric optics and wherein the cameras of the first array of cameras are aligned with one another along an axis perpendicular to a direction of workpiece motion and wherein the cameras of the first array of cameras have fields of view that overlap one another.

3. The optical inspection system of claim 1, wherein the first array of cameras includes non-telecentric optics and wherein the cameras of the second array of cameras are aligned with one another along an axis perpendicular to the direction of workpiece motion, but spaced from the first plurality of cameras in a direction of the workpiece motion.

4. The optical inspection system of claim 1, wherein:
the first array of cameras has telecentric optics, and wherein the cameras of the first array of cameras are aligned with one another along an axis perpendicular to a direction of workpiece motion, and have fields of view that do not overlap with one another; and
further comprising a third array of cameras having telecentric optics, and wherein the cameras of the third array of cameras are aligned with one another along an axis perpendicular to a direction of workpiece motion, and have fields of view that do not overlap with one another, wherein the first and third arrays of cameras have fields of view that are staggered;
wherein the second array of cameras has telecentric optics, and wherein the cameras of the second array of cameras are aligned with one another along an axis perpendicular to a direction of workpiece motion, and have fields of view that do not overlap with one another; and
further comprising a fourth array of cameras having telecentric optics, and wherein the cameras of the fourth array of cameras are aligned with one another along an axis perpendicular to a direction of workpiece motion, and have fields of view that do not overlap with one another, wherein the second and fourth arrays of cameras have fields of view that are staggered.

5. The optical inspection system of claim 1, and further comprising an encoder operably coupled to the workpiece transport to provide an indication of workpiece motion to the processing device.

6. The optical inspection system of claim 5, wherein the indication has a resolution of approximately 100 microns.

7. The optical inspection system of claim 1, wherein the illuminator includes at least one arc lamp.

8. The optical inspection system of claim 1, wherein the illuminator includes at least one light emitting diode.

9. The optical inspection system of claim 1, wherein the light pipe includes a plurality of reflective sidewalls.

10. The optical inspection system of claim 1, wherein the at least one reflective sidewall includes a curved reflective surface that preserves illumination elevation angle while mixing illumination azimuthally.

11. The optical inspection system of claim 1, wherein the illuminator includes at least one mirror disposed to reflect at least a portion of illumination to a desired source elevation angle.

12. The optical inspection system of claim 11, wherein the at least one mirror is angled to reflect the portion of illumination toward the at least one reflective sidewall at the desired elevation angle.

13. The optical inspection system of claim 1, wherein the illuminator includes an illumination mixing chamber disposed proximate the second end, and wherein the mixing chamber and the light pipe are separated by a translucent diffuser having at least one diffuser aperture aligned with each respective at least one second end aperture.

14. The optical inspection system of claim 13, wherein a first light source is configured to introduce strobed illumination into the mixing chamber.

15. The optical inspection system of claim 14, wherein a second light source is configured to introduce strobed illumination into the light pipe between the diffuser and the first end.

16. The optical inspection system of claim 15, and further comprising a third light source configured to introduce additional illumination into the light pipe between the diffuser and the first end.

17. The optical inspection system of claim 1, wherein the processing device includes a high-speed data transfer bus to provide the first, second, third and fourth pluralities of images to the other device.

18. The optical inspection system of claim 17, wherein the processing device is configured to simultaneously acquire and store images from the first and second arrays of cameras while providing images to the other device.

19. The optical inspection device of claim 18, wherein the high-speed data transfer bus operates in accordance with the peripheral component interconnect express (PCIe) bus.

20. The optical inspection system of claim 1, wherein the other device is configured to provide an inspection result relative to the feature on the workpiece based, at least in part, upon the first, second, third and fourth pluralities of images.

21. The optical inspection system of claim 1, and further comprising a structured light projector configured to project structured light onto the workpiece.

22. The optical inspection system of claim 21, wherein the structured light projector is configured to project a random dot pattern.

23. The optical inspection system of claim 21, wherein the structured light projector is configured to project at least one laser stripe.

24. The optical inspection system of claim 21, wherein the structured light projector is configured to project at least one sinusoidal fringe onto the workpiece.

25. The optical inspection system of claim 1, wherein the first and second arrays of cameras are angled with respect to a surface normal to the workpiece.

26. The optical inspection system of claim 1, wherein the first array of cameras is oriented to view the workpiece from an angle that is substantially perpendicular to a surface of the workpiece.

27. A method of inspecting an article of manufacture, the method comprising:
generating relative motion between the article of manufacture and a pair of camera arrays;
simultaneously acquiring a first set of images from a first camera array of the pair of camera arrays through a light pipe during the relative motion and while strobing a first illumination field type upon the article of manufacture;
generating at least a first stitched image with the first set of acquired images;
acquiring a second set of images from the second camera array through the light pipe while strobing the first illumination field type upon the article of manufacture;
generating at least a second stitched image from the second set of images acquired from the second camera array; and
determining the inspection result relative to the article of manufacture based, at least in part, upon the first and second stitched images.

28. The method of claim 27, and further comprising:
simultaneously acquiring a third set of images from the first camera array of the pair of camera arrays through a light pipe during the relative motion and while strobing a second illumination field type upon the article of manufacture;
generating at least a third stitched image with the third set of acquired images;
acquiring a fourth set of images from the second camera array through the light pipe while strobing the second illumination field type upon the article of manufacture;
generating at least a fourth stitched image from the fourth set of images acquired from the second camera array; and
determining the inspection result relative to the article of manufacture based, at least in part, upon the first, second, third and fourth stitched images.

29. The method of claim 28, wherein the first illumination field type is darkfield.

30. The method of claim 29, wherein the second illumination field type is cloudy day.

31. The method of claim 29, wherein the second illumination field type is brightfield.

32. The method of claim 28, wherein the first illumination field type is structured illumination.

33. The method of claim 28, wherein the first illumination field type is backlight.

34. The method of claim 33, wherein the backlight has a near-infrared wavelength.

35. The method of claim 28, wherein the first and second illumination field types are energized alternately.

36. The method of claim 27, wherein the image stitching is used to correct for positional error of the article of manufacture.

37. The method of claim 27, wherein stitching is used to correct for workpiece warpage.

38. The method of claim 27, and further comprising providing at least some images to an other device while collecting images from the pair of camera arrays.

39. The method of claim 27, wherein the pair of camera arrays are arranged to view the article stereoscopically, and wherein the method further comprises calculating three dimensional surface information based upon at least one of the first and second sets of images.

40. The method of claim 39, wherein the inspection result is based on two dimensional and three dimensional image data.

41. The method of claim 27, wherein the article of manufacture is a solar cell.

42. The method of claim 41, wherein the article of manufacture is a solar cell and wherein the method further comprises establishing a coordinate frame using solar cell fiducial marks.

43. The method of claim 41, wherein the inspection result is indicative of at least one of collector finger height, collector finger width, and collector finger registration.

44. The method of claim 41, wherein the inspection result is indicative of solar cell bowing.

45. The method of claim 41, wherein the inspection result is indicative of solar cell wafer geometry.

46. The method of claim 41, wherein the inspection result is indicative of the presence of chips in the solar cell.

47. The method of claim 41, wherein the inspection result is indicative of the presence of cracks in the solar cell.

* * * * *